United States Patent [19]
Mizuta et al.

[11] Patent Number: 5,550,290
[45] Date of Patent: Aug. 27, 1996

[54] BENZIDINE DERIVATIVE AND ELECTROPHOTOSENSITIVE MATERIAL USING THE SAME

[75] Inventors: Yasufumi Mizuta; Masashi Tanaka; Nariaki Muto; Toshiyuki Fukami; Hideo Nakamori; Mikio Kakui; Sakae Saito; Hiroshi Shiomi; Keisuke Sumida; Maki Uchida, all of Osaka, Japan

[73] Assignee: Mita Industrial Co. Ltd., Osaka, Japan

[21] Appl. No.: 314,375

[22] Filed: Sep. 28, 1994

[30] Foreign Application Priority Data

| | | | |
|---|---|---|---|
| Oct. 13, 1993 | [JP] | Japan | 5-256089 |
| Oct. 13, 1993 | [JP] | Japan | 5-256090 |
| Oct. 14, 1993 | [JP] | Japan | 5-257207 |
| Oct. 14, 1993 | [JP] | Japan | 5-257209 |
| Dec. 3, 1993 | [JP] | Japan | 5-304437 |
| Dec. 3, 1993 | [JP] | Japan | 5-304438 |
| Apr. 8, 1994 | [JP] | Japan | 6-070422 |
| Apr. 8, 1994 | [JP] | Japan | 6-070423 |
| Apr. 8, 1994 | [JP] | Japan | 6-070424 |
| Apr. 8, 1994 | [JP] | Japan | 6-070425 |
| Apr. 8, 1994 | [JP] | Japan | 6-070426 |
| Apr. 8, 1994 | [JP] | Japan | 6-070427 |

[51] Int. Cl.$^6$ .................. C07C 211/54; C07C 217/92
[52] U.S. Cl. ........................................... 564/309
[58] Field of Search ............................. 564/309

[56] References Cited

U.S. PATENT DOCUMENTS

| | | | |
|---|---|---|---|
| 4,925,759 | 5/1990 | Hanatani et al. | 430/59 |
| 4,933,245 | 12/1990 | Akasaki et al. | 430/59 |
| 5,213,926 | 5/1993 | Hanatani et al. | 430/59 |
| 5,272,031 | 12/1993 | Hanatani et al. | 430/59 |
| 5,352,834 | 10/1994 | Morishita et al. | 564/309 |

FOREIGN PATENT DOCUMENTS

| | | |
|---|---|---|
| 0318916 | 6/1989 | European Pat. Off. . |
| 0475676 | 3/1992 | European Pat. Off. . |

OTHER PUBLICATIONS

Patent Abstract of Japan vol. 13, No. 395 of Sep. 4, 1989 concerning JPA 01 142 647 dated Jun. 5, 1989.
Patent Abstract of Japan vol. 13, No. 395 of Sep. 1989 concerning JPA 01 142 644 dated Jun. 5, 1989.
Database WPI Week 9051, JP A–2 277 071 Nov. 13, 1990.

*Primary Examiner*—Richard L. Raymond
*Attorney, Agent, or Firm*—Beveridge, DeGrandi, Weilacher & Young, LLP

[57] ABSTRACT

The present invention relates to a benzidine derivative represented by the general formula (1):

wherein $R^1$ to $R^6$, m and n are as defined in the present specification. The benzidine derivative improves durability and heat resistance of a membrane containing the same while maintaining high hole transferring capability. Therefore, an electrophotosensitive material, which comprises a photosensitive layer containing the benzidine derivative, has high sensitivity and is superior in durability and heat resistance.

9 Claims, 11 Drawing Sheets

BENZIDINE DERIVATIVE AND ELECTROPHOTOSENSITIVE MATERIAL USING THE SAME

BACKGROUND OF THE INVENTION

The present invention relates to a novel benzidine derivative which is suitably used as a charge transferring material, particularly hole transferring material in applications such as solar battery, electroluminescent device, electrophotosensitive material and the like, and an electrophotosensitive material using the same.

As the charge transferring material, there have been known various organic compounds such as carbazole compound, oxadiazole compound, pyrazoline compound, hydrazone compound, stilbene compound, phenylenediamine compound, benzidine compound and the like.

These charge transferring materials are normally used in a state where they are dispersed in a membrane of a suitable binding resin. In case of the electrophotosensitive material, for example, so-called organic photosensitive materials (OPC) such as single-layer type electrophotosensitive material comprising a single-layer type photosensitive layer wherein the above charge transferring material and a charge generating material which generates a charge due to light irradiation are dispersed in a binding resin, multi-layer type electrophotosensitive material comprising a charge transferring layer containing the above electric transferring material and a charge generating layer containing a charge generating material, etc. are normally used. Such an organic photosensitive material has an advantage that it is superior in processability and can be easily produced, and which offers a great degree of freedom for design of performance.

Among these compounds, there can be suitably used a 3,3'-dimethylbenzidine derivative represented by the formula:

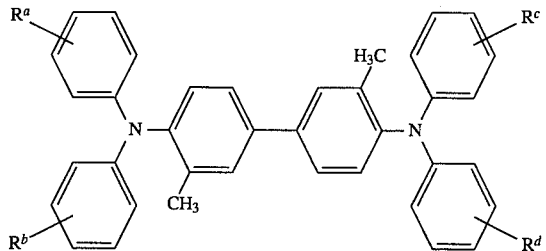

wherein $R^a$, $R^b$, $R^c$ and $R^d$ are same or different and indicate a hydrogen atom, a lower alkyl group, a lower alkoxy group or a chlorine atom, which belongs to the benzidine derivative, because of its high hole transferring capability and good compatibility with the binding resin (see Japanese Laid-Open Patent Publication No. 5-210099).

However, the above 3,3'-dimethylbenzidine derivative has such a disadvantage that it has generally low melting point (about 180° C. or less) and therefore a glass transition temperature (Tg) of a membrane comprising the 3,3'-dimethylbenzidine derivative dispersed in the binding resin becomes low, which results in deterioration of durability, heat resistance and the like.

In case of the electrophotosensitive material, for example, the steps of ① charging of the surface of the electrophotosensitive material due to corona discharge, ② formation of a electrostatic latent image due to exposure, ③ toner development of the electrostatic latent image due to adhesion of toner, ④ image transfer of the toner image to a paper and ⑤ removal of the residual toner on the surface of the electrophotosensitive material after image transfer are repeated. For cleaning the residual toner, there can be used a cleaning blade which is pressure-contacted on the surface of the electrophotosensitive material. Therefore, in an electrophotosensitive material using a conventional benzidine derivative, a pressure welding dent is formed at the part where the cleaning blade has been pressure-contacted when the image forming apparatus is stopped, thereby causing various failures of image. Further, when operating the image forming apparatus, a temperature of the interior of the apparatus increases to about 50° C. and therefore a recess is formed on the surface of the electrophotosensitive material, thereby causing various failures of image.

THE SUMMARY OF THE INVENTION

It is a main object of the present invention is to provide a novel benzidine derivative which is superior in compatibility with the binding resin while maintaining high hole transferring capability, and which improves durability, heat resistance, etc. of a membrane formed by dispersing it in a binding resin.

It is another object of the present invention to provide a high-performance electrophotosensitive material using the above benzidine derivative as a hole transferring material, which has high sensitivity as well as excellent durability and heat resistance.

In order to solve the above problems, the present inventors have studied to increase the melting point of the benzidine derivative, and they carried out molecular designing according to the policy. As a result, it has been found that the melting point of the benzidine derivative can be increased while maintaining high hole transferring capability and good compatibility with the binding resin by satisfying at least one of the following conditions, and the present invention has been accomplished.

① At least two out of four outer phenyl groups of the benzidine derivative are substituted with two or three alkyl groups.

② Two out of four outer phenyl groups of the benzidine derivative are-substituted with straight-chain or branched alkyl groups having 3 to 5 carbon atoms.

③ Substituents such as alkyl group are introduced in 3,3'- and 5,5'-positions of biphenyl as a center skeleton of the benzidine derivative.

④ Substituents such as alkyl group are introduced in 2,2'- and 5,5'-positions of biphenyl as a center skeleton of the benzidine derivative.

⑤ Phenyl groups are bonded to para-positions of two or four outer phenyl groups of the benzidine derivative to form biphenylyl groups, thereby imparting stretch of space to a π-electron conjugate system.

That is, benzidine derivatives of the present invention are represented by the following general formulas (1) to (5):

I. the general formula (1):

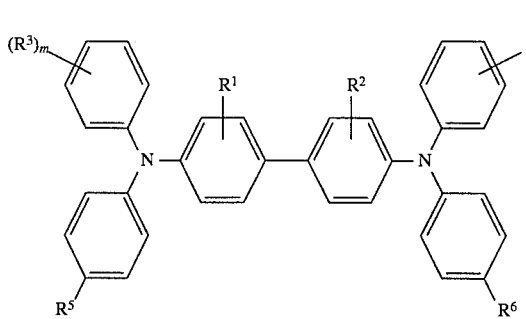

wherein $R^1$ and $R^2$ are the same or different and indicate a hydrogen atom or an alkyl group; $R^3$ and $R^4$ are the same or different and indicate an alkyl group, an alkoxy group or a halogen atom; $R^5$ and $R^6$ are the same or different and indicate an alkyl group having 3 to 5 carbon atoms or an aryl group which may contain a substituent; and m and n are the same or different and indicate an integer of 2 or 3, preferably the general formula (1'):

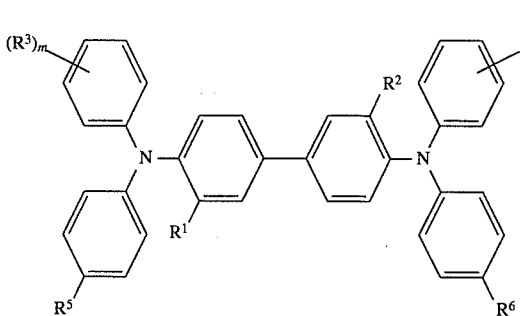

wherein $R^1$, $R^2$, $R^3$, $R^4$, $R^5$, m and n are as defined above;

II. the general formula (2):

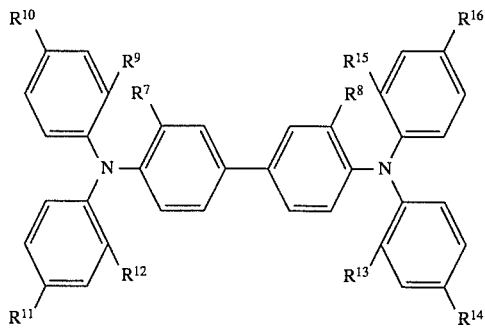

wherein $R^7$, $R^8$, $R^9$, $R^{10}$, $R^{11}$, $R^{12}$, $R^{13}$, $R^{14}$, $R^{15}$ and $R^{16}$ are the same or different and indicate an alkyl group, an alkoxy group or a halogen atom;

III. the general formula (3):

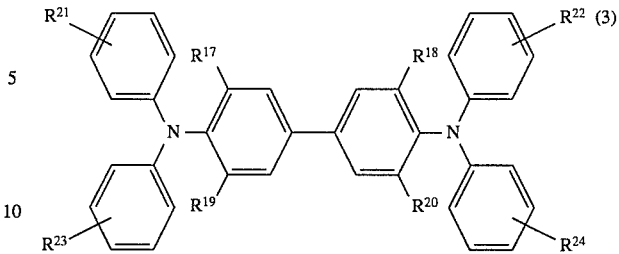

wherein $R^{17}$, $R^{18}$, $R^{19}$ and $R^{20}$ are the same or different and indicate an alkyl group or am alkoxy group; $R^{21}$ and $R^{22}$ are the same or different and indicate a hydrogen atom, an alkyl group, an alkoxy group or a halogen atom; and $R^{23}$ and $R^{24}$ are the same or different and indicate a hydrogen atom, an alkyl group or an aryl group which may contain a substituent, preferably the general formula (3'):

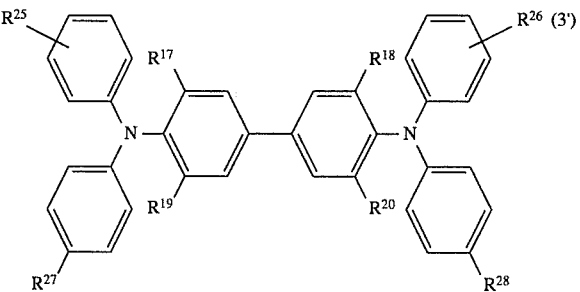

wherein $R^{17}$, $R^{18}$, $R^{19}$ and $R^{20}$ are as defined above; $R^{25}$ and $R^{26}$ are the same or different and indicate a hydrogen atom or an alkyl group; and $R^{27}$ and $R^{28}$ are the same or different and indicate an alkyl group having 3 to 5 carbon atoms or an aryl group which may contain a substituent;

IV. the general formula (4):

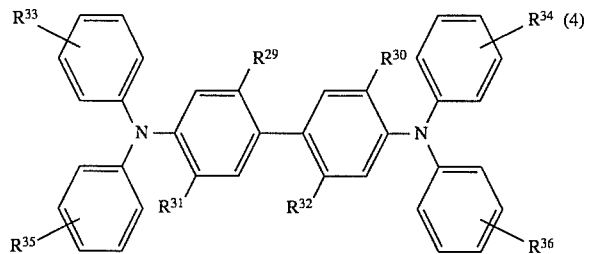

wherein $R^{29}$, $R^{30}$, $R^{31}$ and $R^{32}$ are the same or different and indicate an alkyl group or an alkoxy group; $R^{33}$ and $R^{34}$ are the same or different and indicate an alkyl group, an alkoxy group or a halogen atom; and $R^{35}$ and $R^{36}$ are the same or different and indicate an alkyl group having 3 to 5 carbon atoms; and V. the general formula (5):

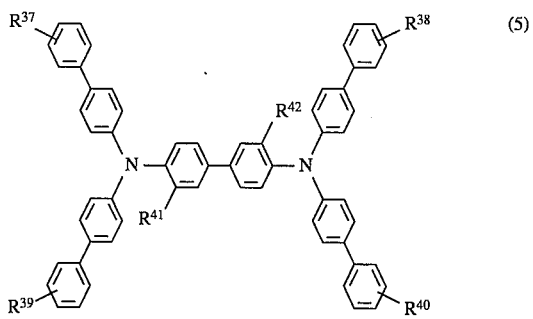

wherein $R^{37}$, $R^{38}$, $R^{39}$ and $R^{40}$ are the same or different and indicate a hydrogen atom or an alkyl group; and $R^{41}$ and $R^{42}$ are the same or different and indicate an alkyl group.

The electrophotosensitive material of one embodiment of the present invention comprises a conductive substrate, and a photosensitive layer provided on the conductive substrate, said photosensitive layer containing at least one of benzidine derivatives represented by the above general formulas (1) to (5) as a hole transferring material.

The electrophotosensitive material of another embodiment of the present invention is a positively-charged type electrophotosensitive material comprising a conductive substrate, and a single photosensitive layer provided on the onductive substrate, said single photosensitive layer containing a benzidine derivative represented by the general formula (6):

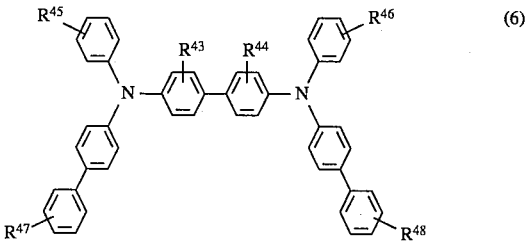

wherein $R^{43}$, $R^{44}$, $R^{45}$, $R^{46}$, $R^{47}$ and $R^{48}$ are the same or different and indicate a hydrogen atom, an alkyl group, an alkoxy group or a halogen atom, as a hole transferring material.

DETAILED DESCRIPTION OF THE INVENTION

Figure 1:
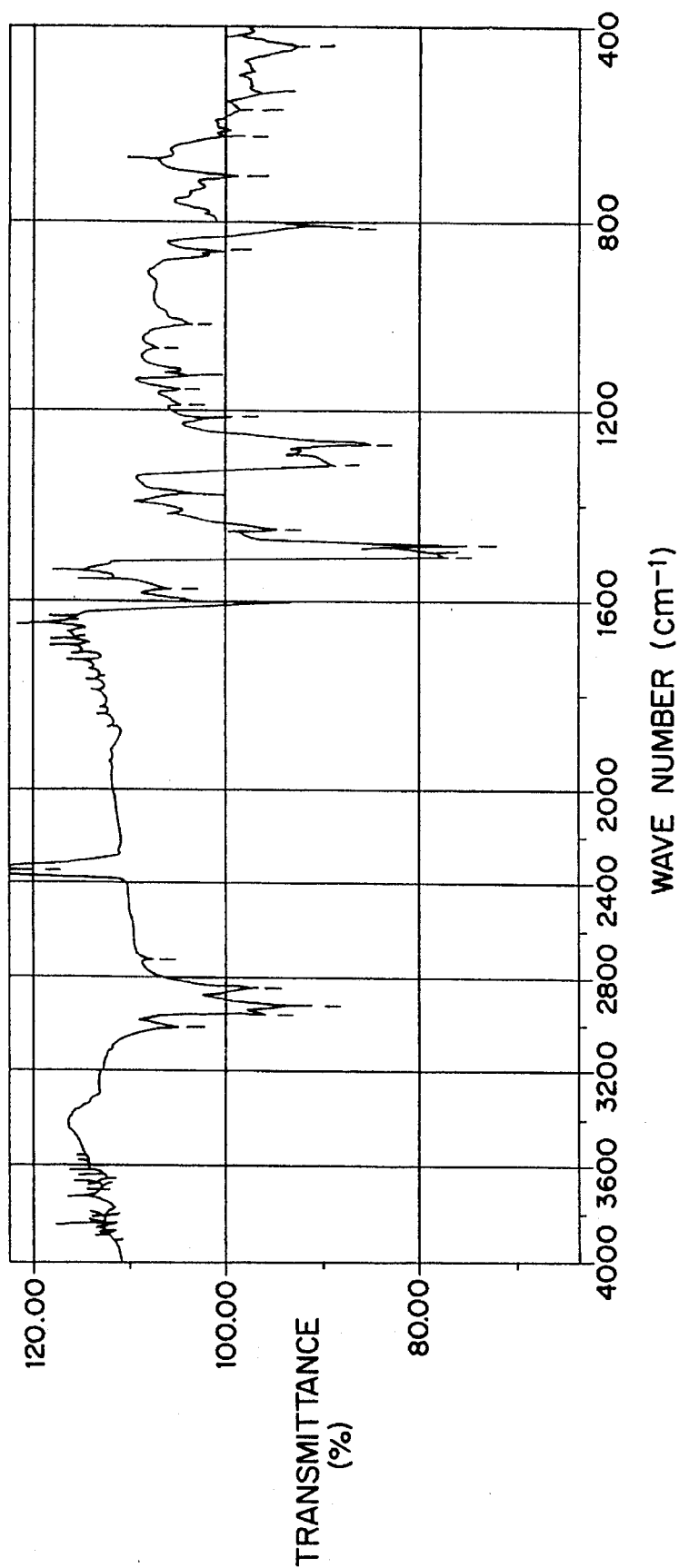
FIGS. 1 to 11 are graphs illustrating the results of infrared spectroscopic analysis of benzidine derivatives obtained in Synthesis Examples 1, 2, 4, 7, 8, 11, 17, 18, 23, 25 and 28, respectively.

Carbon atom of alkyl groups represented by the substituents $R^5$, $R^6$, $R^{27}$, $R^{28}$, $R^{35}$ and $R^{35}$ in the above general formulas (1), (3') and (4) are, as described above, limited to 3 to 5 carbon atoms. When the number of the carbon atom of the alkyl group is less than 3, good compatibility with the binding resin can not be obtained. On the other hand, when the number of the carbon atom of the alkyl group exceeds 5, hole transferring capability is deteriorated.

Examples of the alkyl group having 3 to 5 carbon atoms include straight-chain or branched alkyl groups such as propyl group (n-Pr), isopropyl group (i-Pr), butyl group (n-Bu), isobutyl group (i-Bu), tert-butyl group (t-Bu), pentyl group and the like.

Examples of the other alkyl group of which number of the carbon atom is not specifically limited include lower alkyl groups having 1 to 6 carbon atoms such as methyl group, ethyl group, propyl group, isopropyl group, butyl group, isobutyl group, tert-butyl group, pentyl group, hexyl group and the like. Particularly, methyl and ethyl groups are suitably used.

The symbols m and n which define the number of substituents in the general formula (1) are limited to 2 or 3, as described above. When the number of substituents $R^3$ and $R^4$ is 1, the melting point of the benzidine derivative can not be improved. Further, when the number of substituents is not less than 4, good compatibility with the binding resin is not obtained.

Examples of the alkoxy group include straight-chain or branched alkoxy groups having 1 to 6 carbon atoms such as methoxy group, ethoxy group, propoxy group, isopropoxy group, butoxy group, tert-butoxy group, pentyloxy group, hexyloxy group and the like.

Examples of the aryl group include phenyl group, tolyl group, naphthyl group, biphenyl group, anthryl group, phenanthryl group and the like. Further, examples of the substituent with which the aryl group may be substituted include alkyl group, alkoxy group, halogen atom and the like.

Examples of the halogen atom include chlorine, bromine, iodine, fluorine and the like.

Examples of the benzidine derivative represented by the general formula (1) include compounds represented by the following formulas (1-a) to (1-j).

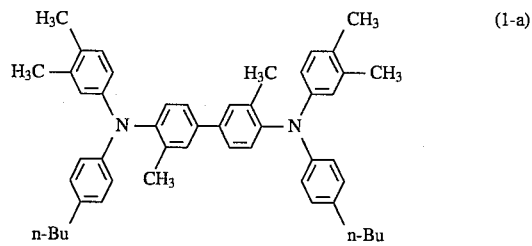

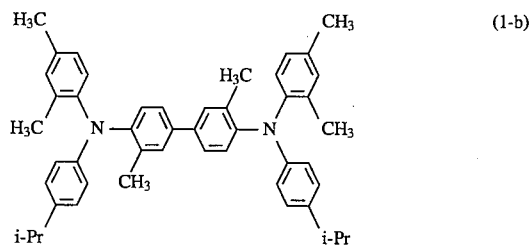

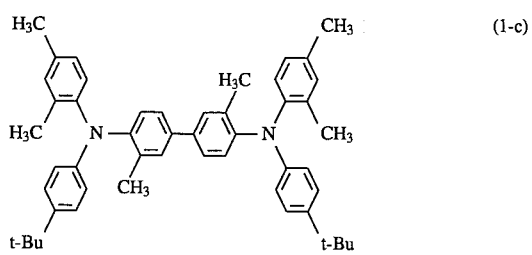

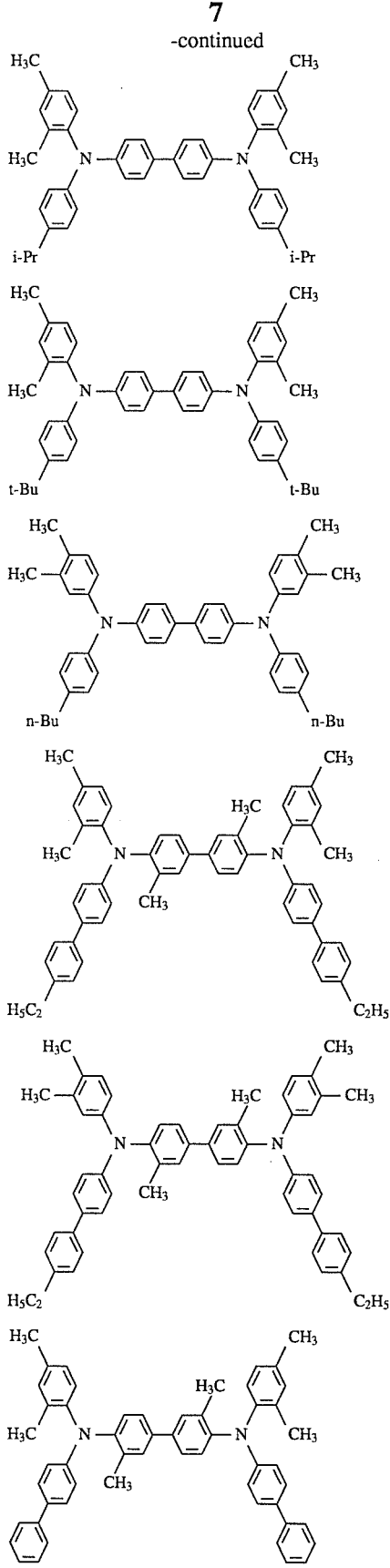

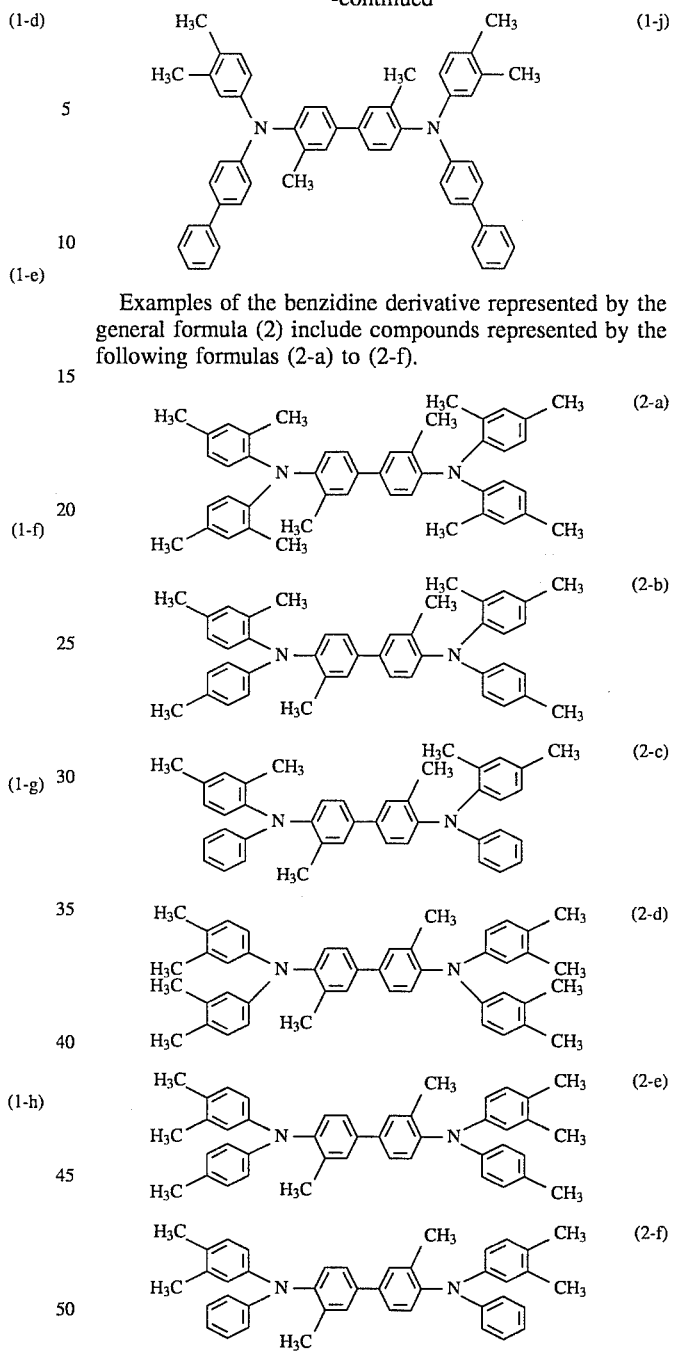

Examples of the benzidine derivative represented by the general formula (2) include compounds represented by the following formulas (2-a) to (2-f).

Symmetrical compounds wherein the substituents $R^{21}$ to $R^{24}$ are the same and their substitution positions are the same and, further, the substituents $R^{17}$ to $R^{20}$ are the same are also included in the benzidine derivative represented by the general formula (3), but unsymmetrical compounds are more preferable, taking performances as the charge transferring material (e.g. compatibility with the binding resin, charge transferring capability, etc.) into consideration. The term "unsymmetrical compound" used herein means those which satisfy at least one of conditions:

① the substituents $R^{21}$ to $R^{24}$ are different;

② substitution positions of the substituents $R^{21}$ to $R^{24}$ are different; and ③ the substituents $R^{17}$ to $R^{20}$ are different. Particularly, those which satisfy the condition ① (the substituents $R^{21}$ to $R^{24}$ are different) are preferable in view of the above performances as the charge transferring material or ease of manufacturing.

Examples of the unsymmetrical benzidine compound include compounds wherein all of the substituents $R^{17}$ to $R^{20}$ are methyl groups and 4-positions of phenyl groups are substituted with all of the substituents $R^{21}$ to $R^{24}$, and the substituents $R^{21}$ and $R^{22}$ are hydrogen atoms or the same alkyl groups and, further, the substituents $R^{23}$ and $R^{24}$ are the same alkyl groups and are different from the above substituents $R^{21}$ and $R^{22}$.

Examples of the benzidine derivative represented by the general formula (3) include compounds represented by the following formulas (3-a) to (3-c). As is apparent from these formulas, there are compounds wherein the substituents $R^{21}$ and $R^{22}$ are hydrogen atoms and the substituents $R^{23}$ and $R^{24}$ are alkyl groups such as methyl group, or compounds wherein the substituents $R^{21}$ and $R^{22}$ are methyl groups and the substituents $R^{23}$ and $R^{24}$ are alkyl groups having 2 or more carbon atoms, such as tert-butyl group, n-butyl group and the like. Among compounds wherein all of the substituents $R^{21}$ to $R^{24}$ are alkyl groups, the more difference of the number of carbon atoms between alkyl groups of the substituents $R^{21}$ and $R^{22}$ and those of the substituents $R^{23}$ and $R^{24}$ is, the more preferable, taking charge transferring capability, compatibility with the binding resin, etc. into consideration. Further, —$C_4H_9$ in the formula (3-c) indicates a n-butyl group.

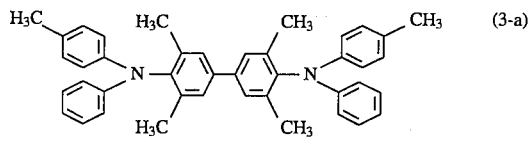
(3-a)

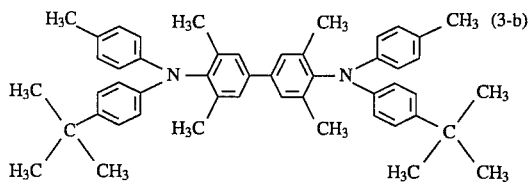
(3-b)

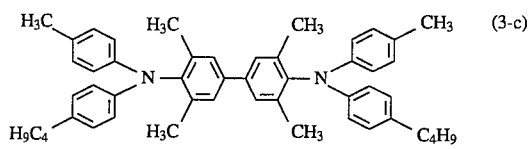
(3-c)

On considering these conditions, there can be given N,N'-di(4-methylphenyl)-N,N'-di(4-tert-butylphenyl)-3,3', 5,5'-tetramethylbenzidine represented by the formula (3-b) as a most preferable benzidine derivative.

Further, examples of the other benzidine derivative represented by the general formula (3) include compounds represented by the following formulas (3-d) to (3-f).

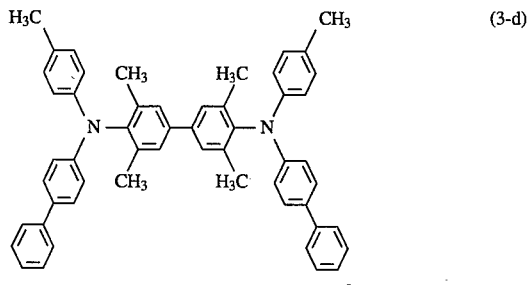
(3-d)

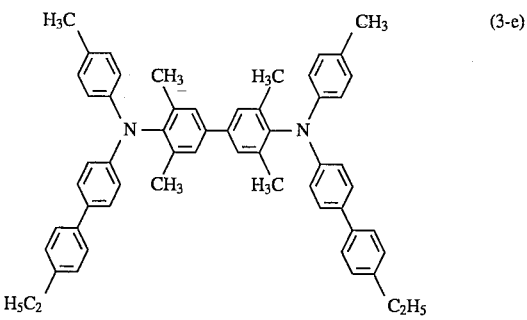
(3-e)

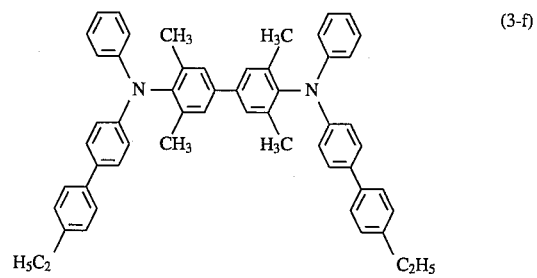
(3-f)

Examples of the benzidine derivative represented by the general formula (4) include compounds represented by the following formulas (4-a) and (4-b).

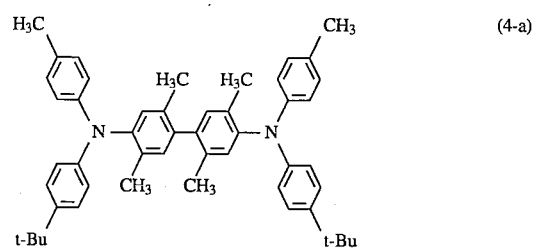
(4-a)

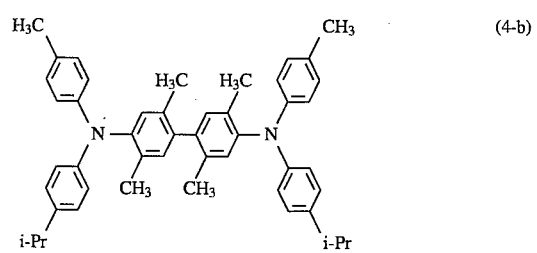
(4-b)

Examples of the benzidine derivative represented by the general formula (5) include compounds represented by the following formulas (5-a) to (5-c).

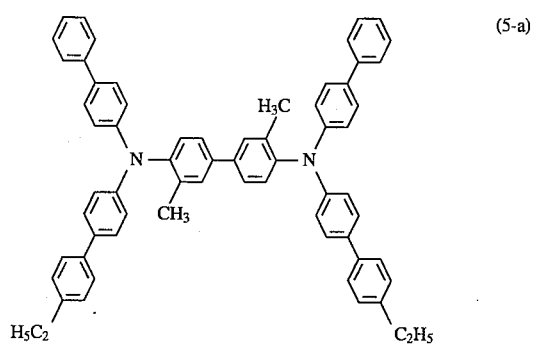
(5-a)

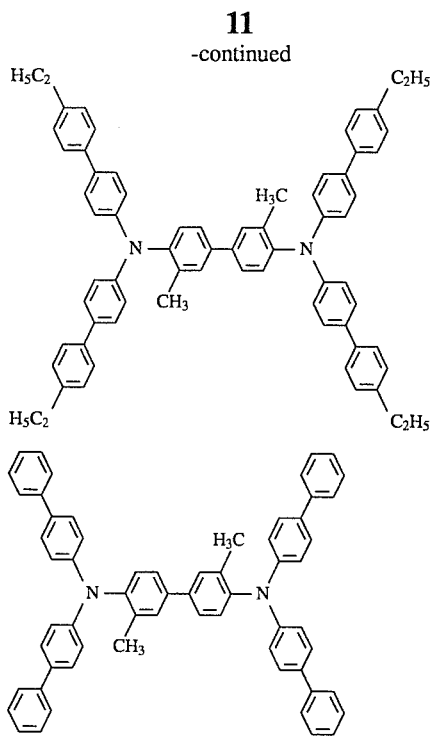

(5-b)

(5-c)

In the benzidine derivative represented by the general formula (6), it is preferred that phenyl groups bonded to nitrogen atoms of a benzidine skeleton are substituted with the substituents $R^{45}$ and $R^{46}$ at 4-positions (para-positions). In case of a biphenylyl group, nitrogen atoms can bond to any position of 2'-position to 4'-position, but those wherein nitrogen atoms bond to 4-positions are preferred. The substituents $R^{47}$ and $R^{48}$ with which biphenyl groups are substituted can bond to 2- to 6-positions of biphenyl groups, but those wherein the substituents $R^{47}$ and $R^{48}$ bond to 4-positions are preferred.

The benzidine derivative of the present invention can be synthesized by various methods. For example, the benzidine derivative of the above formula (1-a) can be synthesized according to the following reaction scheme.

Firstly, N,N'-diacetyl-3,3'-dimethylbenzidine represented by the following formula (7) and 3,4-dimethyliodobenzene represented by the formula (8) are mixed together with copper powder, copper oxide or copper halide in a molar ratio of 1:2 and the mixture was reacted in the presence of a basic substance to give N,N'-diacetyl-N,N'-bis(3,4-dimethylphenyl)-3,3'-dimethylbenzidine represented by the formula (9).

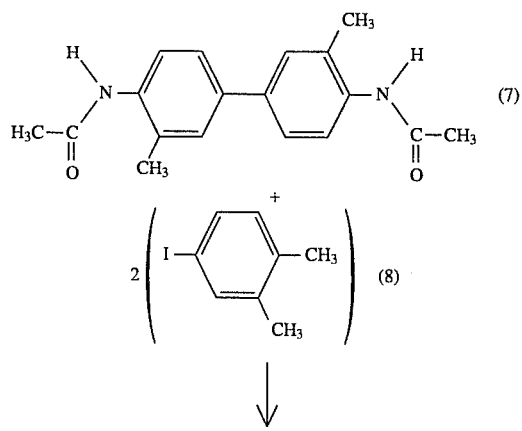

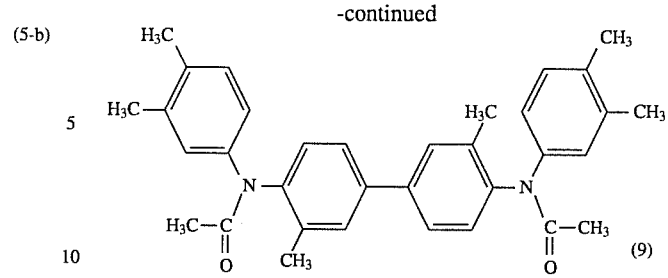

Then, N,N'-diacetyl-N,N'-bis(3,4-dimethylphenyl)-3,3'-dimethylbenzidine represented by the formula (9) is subjected to a deacetylation reaction in the presence of an amide-decomposition catalyst such as acid to give N,N'-bis(3,4-dimethylphenyl)-3,3'-dimethylbenzidine represented by the following formula (10), which is reacted with 4-n-butyliodobenzene in a molar ratio of 1:2 to give a benzidine derivative of the formula (1-a).

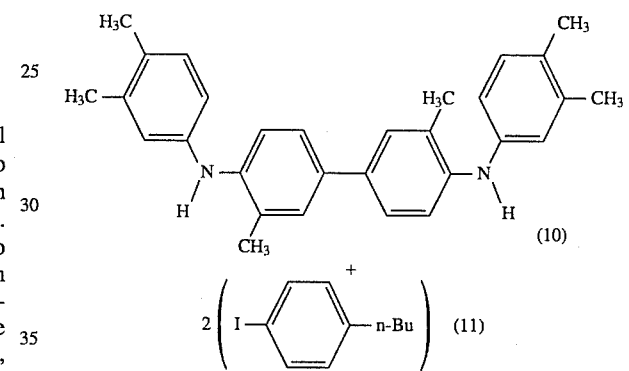

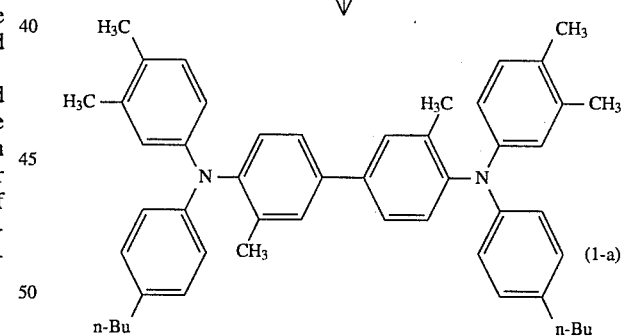

Further, the benzidine derivative of the present invention can also be synthesized by the following reaction scheme in place of the above synthesis method. The following reaction scheme illustrates a synthesis method of the benzidine derivative of the formula (1-d).

Firstly, 4,4'-diiodobiphenyl represented by the following formula (7') and p-isopropylacetanilide represented by the formula (8') are mixed together with copper powder, copper oxide or copper halide in a molar ratio of 1:2 and the mixture was reacted in the presence of a basic substance to give N,N'-diacetyl-N,N'-bis(4-isopropylphenyl)benzidine represented by the formula (9').

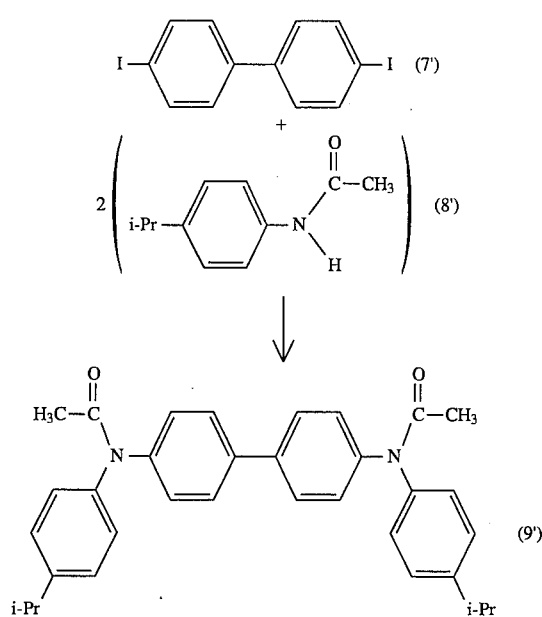

Then, N,N'-diacetyl-N,N'-bis(4-isopropylphenyl)benzidine represented by the above formula (9') is subjected to a deacetylation reaction to give N,N'-bis(4-isopropylphenyl)benzidine represented by the following formula (10'), which is reacted with 2,4-dimethyliodobenzene represented by the formula (10) in a molar ratio of 1:2 according to the same manner as that described above to give a benzidine derivative of the formula (1-d).

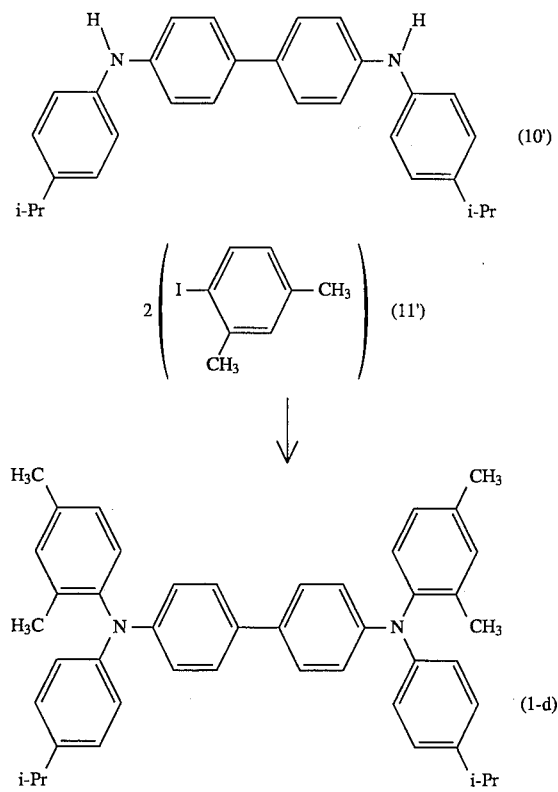

As described above, the benzidine derivative of the present invention is suitably used as a charge transferring material, particularly hole transferring material in applications such as solar battery, electroluminescent material, electrophotosensitive material and the like, and can also be used in other various fields.

The electrophotosensitive material of the present invention comprises a photosensitive layer on a conductive substrate, said photosensitive layer containing one or more sorts of benzidine derivatives represented by the above formulas (1) to (6). The photosensitive layer is classified into two types, i.e. a single-layer type photosensitive layer and a multi-layer type photosensitive layer. The constitution of the present invention can be applied to both photosensitive layers. The benzidine derivative of the general formula (6) is only used for the single-layer type electrophotosensitive material.

The single-layer type photosensitive layer may be obtained by applying a coating solution, which is prepared by dissolving or dispersing at least one of benzidine derivatives represented by the general formulas (1) to (6) as a hole transferring material, a charge generating material and a binding resin in a suitable solvent, on a conductive substrate using a means such as coating, followed by drying.

Further, the multi-layer type photosensitive layer may be obtained by forming a charge generating layer containing a charge generating material on a conductive substrate using a means such as deposition or coating, applying a coating solution containing at least one of benzidine derivatives represented by the general formulas (1) to (5) and a binding resin on the charge generating layer using a means such as coating, followed by drying to form a charge transferring layer. To the contrary, a charge transferring layer may be formed on a conductive substrate and then a charge generating layer may be formed thereon.

Non-limited examples of the charge generating material include powder of inorganic photoconductive materials (e.g. selenium, selenium-tellurium, selenium-arsenic, cadmium sulfide, α-silicon, etc), azo pigments, perylene pigments, anthanthrone pigments, phthalocyanine pigments, indigo pigments, triphenylmethane pigments, therene pigments, toluidine pigments, pyrazoline pigments, quinacridon pigments, dithioketopyrrolopyrrole pigments and the like. These charge generating materials can be used alone or in combination thereof according to the range of sensitivity of the electrophotosensitive material.

The benzidine derivatives represented by the general formulas (1) to (6) as the hole transferring material can be used alone or in combination with the other charge transferring materials which have hitherto been known.

Examples of the other charge transferring material include various electron transferring materials and hole transferring materials.

Examples of the electron transferring material include electron attractive materials such as diphenoxy compounds, benzoquinone compounds, naphthoquinone compounds, malononitrile, thiopyran compounds, tetracyanoethylene, tetracyanoquinodimethane, chloroanil, bromoanil, 2,4,7-trinitro-9-fluorenone, 2,4,5,7-tetranitro-9-fluorenone, 2,4,7-trinitro-9-dicyanomthylenefluorenone, 2,4,5,7-tetranitroxanthone, 2,4,8-trinitrothioxanthone, dinitrobenzene, dinitroanthracene, dinitroacridine, nitroanthraquinone, dinitroanthraquinone, succinic anhydride, maleic anhydride, dibromomaleic anhydride, etc., high-molecular electron attractive materials and the like.

Examples of the hole transferring material include electron donative materials such as nitrogen-containing cyclic compounds and condensed polycyclic compounds which include diamine compounds other than benzidine derivatives represented by the general formulas (1) to (6); diazole compounds such as 2,5-bis(4-methylaminophenyl)-1,3,4-oxadiazole, etc.; styryl compounds such as 9-(4-diethylaminostyryl)anthracene, etc.; carbazole compounds such as polyvinyl carbazole, etc.; pyrazoline compounds such as 1-phenyl-3-(p-dimethylaminophenl)pyrazoline, etc.; hydrazone compounds; triphenylamine compounds; indol compounds; oxazole compounds; isooxazole compounds, thiazole compounds; thiadiazole compounds; imidazole compounds; pyrazole compounds; triazole compounds and the like.

Further, when using a charge transferring material having film forming properties such as polyvinyl carbazole, the binding resin is not necessarily required.

Examples of the binding resin include thermoplastic resins such as styrene polymer, styrene-butadiene copolymer, styrene-acrilonitrile copolymer, styrene-maleic acid copolymer, acrylic polymer, styrene-acrylic copolymer, polyethylene, ethylene-vinyl acetate copolymer, chlorinated polyethylene, polyvinyl chloride, polypropylene, vinyl chloride-vinyl acetate copolymer, polyester, alkyd resin, polyamide, polyurethane, polycarbonate, polyarylate, polysulfon, diaryl phthalate resin, ketone resin, polyvinyl butyral resin, polyether resin, etc.; crosslinking thermosetting resins such as silicone resin, epoxy resin, phenol resin, urea resin, melamine resin, etc.; photosetting resins such as epoxyacrylate, urethane-acrylate, etc. These binding resins can be used alone or in combination thereof.

Additives such as sensitizers, fluorene compounds, antioxidants, ultraviolet absorbers, plasticizers, surfactants, leveling agents, etc. can be added to the photosensitive layer, in addition to the above respective components. In order to improve sensitivity of the electrophotosensitive material, there may be used sensitizers such as tert-phenyl, halonaphthoquinones, acenaphthylene, etc. in combination with the charge generating material.

In the multi-layer electrophotosensitive material, the charge generating material constituting the charge generating layer and the binding resin can be used in various proportions. It is preferred that 5 to 1000 parts by weight, particularly 30 to 500 parts by weight of the charge generating material is used, based on 100 parts by weight of the binding resin.

The charge transferring material constituting the charge transferring layer and the binding resin can be used in various proportions within such a range as not to prevent the transmission of the charge and as to prevent the crystallization of the charge transferring material. It is preferred that 10 to 500 parts by weight, particularly 25 to 200 parts by weight of the charge transferring material containing the benzidine derivatives represented by the general formulas (1) to (5) as the hole transferring material is used, based on 100 parts by weight of the binding resin so as to easily transfer the charge generated in the charge generating layer due to light irradiation.

Regarding the thickness of the multi-layer type photosensitive layer, it is preferred that the thickness of the charge generating layer is about 0.01 to 5 μm, particularly about 0.1 to 3 μm and the thickness of the charge transferring layer is about 2 to 100 μm, particularly about 5 to 50 μm.

In the single-layer type electrophotosensitive material, it is suitable that 0.1 to 50 parts by weight, particularly 0.5 to 30 parts by weight of the charge generating material and 10 to 500 parts by weight, particularly 25 to 200 parts by weight of the hole transferring material containing the benzidine derivatives represented by the general formulas (1) to (6) are used, based on 100 parts by weight of the binding resin. When using in combination with the electron transferring material, it is preferred to use the electron transferring material in the amount of 5 to 100 parts by weight, particularly 10 to 80 parts by weight, based on 100 parts by weight of the binding resin. It is preferred that the total amount of the hole transferring and electron transferring materials is 20 to 500 parts by weight, particularly 30 to 200 parts, based on 100 parts by weight of the binding resin.

A barrier layer (undercoat layer) may be formed, in such a range as not to injure the characteristics of the electrophotosensitive material, between the conductive substrate and the photosensitive layer in the single-layer type electrophotosensitive material, or between the conductive substrate and the charge generating layer, between the conductive substrate and the charge transferring layer or between the charge generating layer and the charge transferring layer in the multi-layer type electrophotosensitive material. Further, a protective layer may be formed on the surface of the electrophotosensitive material.

As the conductive substrate on which the above respective layers are formed, various materials having conductivity can be used, and examples thereof include metals such as aluminum, copper, tin, platinum, silver, iron, vanadium, molybdenum, chromium, cadmium, titanium, nickel, palladium, indium, stainless steel, brass, etc.; plastic materials vapor-deposited or laminated with the above metal; glass materials coated with aluminum iodide, tin oxide, indium oxide, etc.

The conductive substrate may be made in the form of a sheet or a drum. The substrate itself may have conductivity or only the surface of the substrate may have conductivity. It is preferred that the conductive substrate has a sufficient mechanical strength when used.

When the above respective layers constituting the electrophotosensitive material are formed by a coating method, the charge generating material, the charge transferring material, the binding resin, etc. may be dispersed/mixed with a suitable solvent by a known method, for example, using a roll mill, a ball mill, an atriter, a paint shaker, a supersonic dispenser, etc. to prepare a coating solution, which is applied by a known means and then allowed to dry.

As the solvent for preparing the coating solution, there can be used various organic solvents, and examples thereof include alcohols such as methanol, ethanol, isopropanol, butanol, etc.; aliphatic hydrocarbons such as n-hexane, octane, cyclohexane, etc.; aromatic hydrocarbons such as benzene, toluene, xylene, etc.; halogenated hydrocarbons such as dichloromethane, dichloroethane, carbon tetrachloride, chlorobenzene, etc.; ethers such as dimethyl ether, diethyl ether, tetrahydrofuran, ethylene glycol dimethyl ether, diethylene glycol dimethyl ether, etc.; ketones such as acetone, methyl ethyl ketone, cyclohexanone, etc.; esters such as ethyl acetate, methyl acetate, etc.; dimethylformaldehyde, dimethylformamide, dimethylsulfoxide, etc. These solvents may be used alone or in combination thereof.

In order to improve dispersibility of the charge transferring material and charge generating material as well as smoothness of the surface of the photosensitive layer, there may be used surfactants, leveling agents, etc.

As described above, the benzidine derivative of the present invention has excellent compatibility with the binding resin while maintaining high hole transferring capability, and has a high melting point in comparison with a conventional benzidine derivative. Therefore, when it is dispersed in the binding resin, the glass transition temperature of the obtained membrane can become higher, thereby improving durability, heat resistance, etc. of the membrane. Accordingly, the benzidine derivative of the present invention can be suitably used as a hole transferring material in applications such as solar battery, electroluminescent device, electrophotosensitive material and the like.

Further, the electrophotosensitive material of the present invention has high sensitivity and is superior in durability and heat resistance.

EXAMPLES

The following Synthesis Examples, Examples and Comparative Examples further illustrate the present invention in detail.

Synthesis Example 1

14.8 G of N,N'-diacetyl-3,3'-dimethylbenzidine, 23.2 g of 3,4-dimethyliodobenzene, 13.8 g of potassium carbonate and 1 g of copper powder were added in 150 ml of nitrobenzene, and the mixture was refluxed with vigorous stirring while a nitrogen gas was bubbling into this reaction system for 24 hours. The water produced in the reaction was removed out of the reaction system by azeotropic distillation with nitrobenzene.

After the reaction solution was cooled, the inorganic substance was filtered off. Further, nitrobenzen was distilled off by steam distillation to give the residue, which was dissolved in 100 ml of tetrahydrofuran together with 10% hydrochloric acid. The solution was deacetylated under reflux for 2 hours to give N,N'-bis(3,4-dimethylphenyl)-3,3'-dimethylbenzidine.

Then, 10.5 g of N,N'-bis(3,4-dimethylphenyl)-3,3'-dimethylbenzidine, 13.0 g of 4-n-butyliodobenzene, 13.8 g of potassium carbonate and 1 g of copper powder were added in 150 ml of nitrobenzene, and the mixture was refluxed with vigorous stirring while a nitrogen gas was blowing into this reaction system for 24 hours. The water produced in the reaction was removed out of the reaction system by azeotropic distillation with nitrobenzene, similar to the above case.

After the reaction solution was cooled, the inorganic substance was filtered off. Further, nitrobenzen was distilled off by steam distillation to give the residue, which was dissolved in 100 ml of cyclohexane and the solution was purified by subjecting to silica gel chromatography and cyclohexane was distilled off to give a white precipitation. Then, the white precipitation was recrystallized from n-hexane to give N,N'-bis(3,4-dimethylphenyl)-N,N'-bis(n-butylphenyl)-3,3'-dimethylbenzidine of the above formula (1-a) as an objective product (8.7 g, yield: 27.3%).

The results of the infrared spectroscopic analysis of the resulting product are shown in FIG. 1.

Elemental analysis (%), Calcd.: C, 87.65; H, 8.26; N, 4.09
Found: C, 87.60; H, 8.24; N, 4.14

Melting point: 180.6° C.

Synthesis Example 2

According to the same manner as that described in Synthesis Example 1 except for using 23.2 g of 2,4-dimethyliodobenzene in place of 3,4-dimethyliodobenzene and using 12.3 g of 4-isopropyliodobenzene in place of 4-n-butyliodobenzene, N,N'-bis(2,4-dimethylphenyl)-N,N'-bis(4-isopropylphenyl)-3,3'-dimethylbenzidine of the above formula (1-b) was obtained (8.4 g, yield:27.2%).

Figure 2:
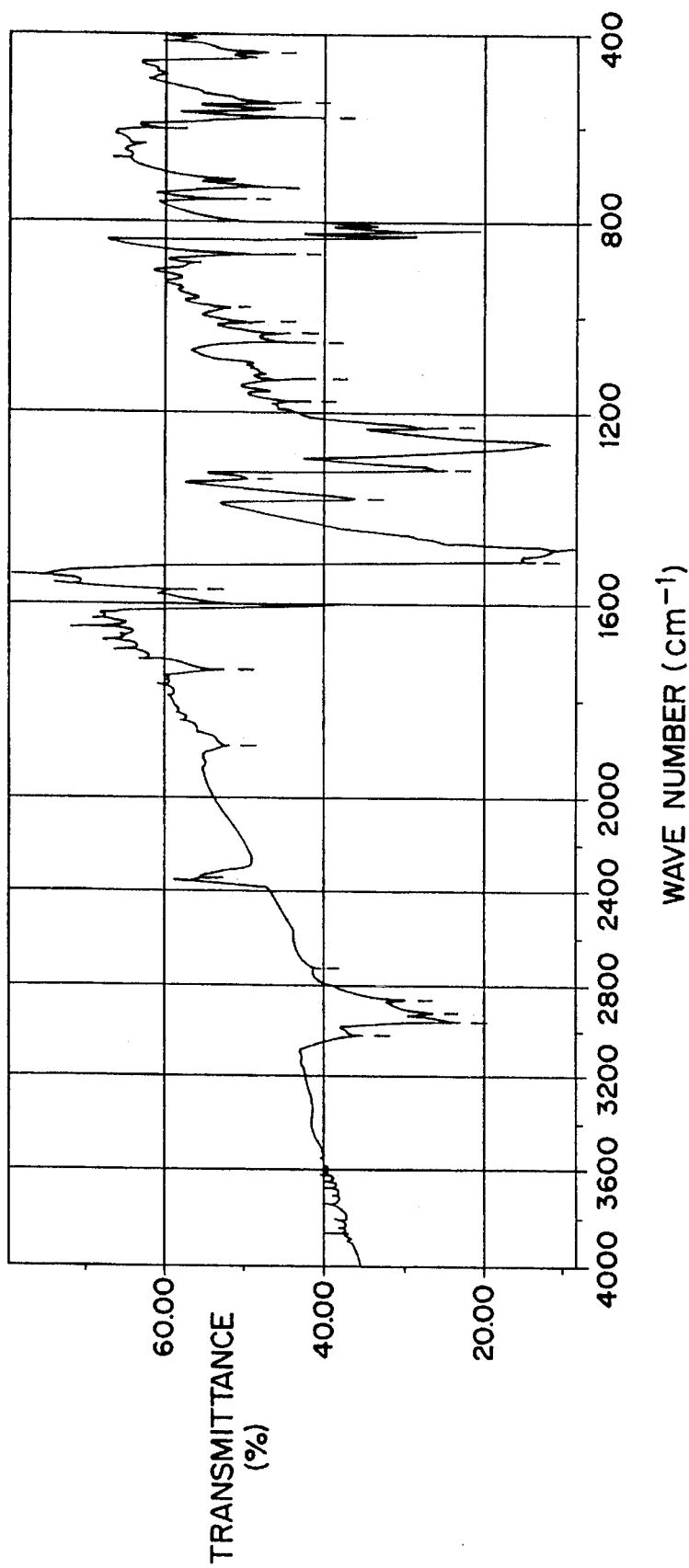

The results of the infrared spectroscopic analysis of the resulting product are shown in FIG. 2.

Elemental analysis (%), Calcd.: C, 87.47; H, 7.99; N, 4.26
Found: C, 87.70; H, 7.97; N, 4.31

Melting point: 182.6° C.

Synthesis Example 3

According to the same manner as that described in Synthesis Example 1, a compound of the above formula (1-c) was obtained using a suitable starting material.

Melting point: 181.9° C.

Synthesis Example 4

20.3 G of 4,4'-diiodobiphenyl, 21.3 g of p-isopropylacetanilide, 13.8 g of potassium carbonate and 1 g of copper powder were added in 150 ml of nitrobenzene, and the mixture was refluxed with vigorous stirring while a nitrogen gas was bubbling into this reaction system for 24 hours. The water produced in the reaction was removed out of the reaction system by azeotropic distillation with nitrobenzene.

After the reaction solution was cooled, the inorganic substance was filtered off. Further, nitrobenzen was distilled off by steam distillation to give the residue, which was dissolved in 100 ml of tetrahydrofuran together with 10% hydrochloric acid. The solution was refluxed for 2 hours to give N,N'-bis(4-isopropylphenyl)benzidine.

Then, 10.5 g of N,N'-bis(4-isopropylphenyl)benzidine, 11.6 g of 2,4-dimethyliodobenzene, 13.8 g of potassium carbonate and 1 g of copper powder were added in 150 ml of nitrobenzene, and the mixture was refluxed with vigorous stirring while a nitrogen gas was bubbling into this reaction system for 24 hours. The water produced in the reaction was removed out of the reaction system by azeotropic distillation with nitrobenzene, similar to the above case.

After the reaction solution was cooled, the inorganic substance was filtered off. Further, nitrobenzen was distilled off by steam distillation to give the residue, which was dissolved in cyclohexane and the solution was purified by subjecting to silica gel chromatography and cyclohexane was distilled off to give a white precipitation. Then, the white precipitation was recrystallized from n-hexane to give N,N'-bis(2,4-dimethylphenyl)-N,N'-bis(4-isopropylphenyl)benzidine of the above formula (1-d) (8.3 g, yield: 29.0%).

Figure 3:
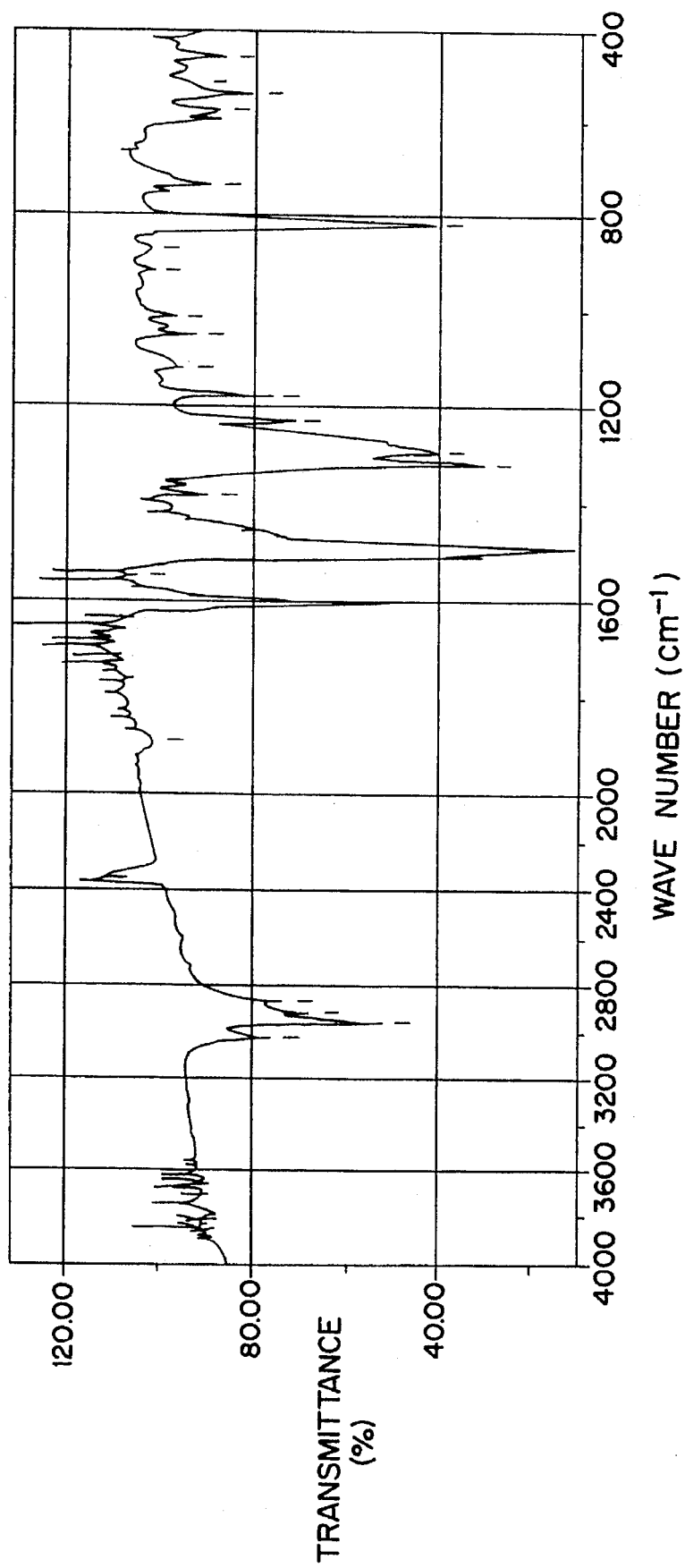

The results of the infrared spectroscopic analysis of the resulting product are shown in FIG. 3.

Elemental analysis (%), Calcd.: C, 87.84; H, 7.71; N, 4.45
Found: C, 87.83; H, 7.66; N, 4.50

Melting point: 187.6° C.

Synthesis Examples 5 and 6

According to the same manner as that described in Synthesis Example 4, compounds of the formulas (1-e) and (1-f) were obtained, respectively, using a suitable starting material.

Melting point of the compound of the formula (1-e): 185.4° C.

Melting point of the compound of the formula (1-f): 183.9° C.

Synthesis Example 7

According to the same manner as that described in Synthesis Example 1, 14.8 g of N,N'-diacetyl-3,3'-diethylbenzidine was reacted with 23.2 g of 2,4-dimethyliodobenzene to give N,N'-bis(2,4-dimethylphenyl)-3,3'-dimethylbenzidine. According to the same manner as that described in Synthesis Example 1, 10.5 g of N,N'-bis(2,4-dimethylphenyl)-3,3'-dimethylbenzidine was reacted with 15.4 g of 4-ethyl-4'-iodophenyl to give N,N'-bis(2,4-dimethylphenyl)-N,N'-bis(4'-ethylbiphenyl-4-yl)-3,3'-dimethylbenzidine of the above formula (1-g) (7.8 g, yield: 21.3%).

Figure 4:
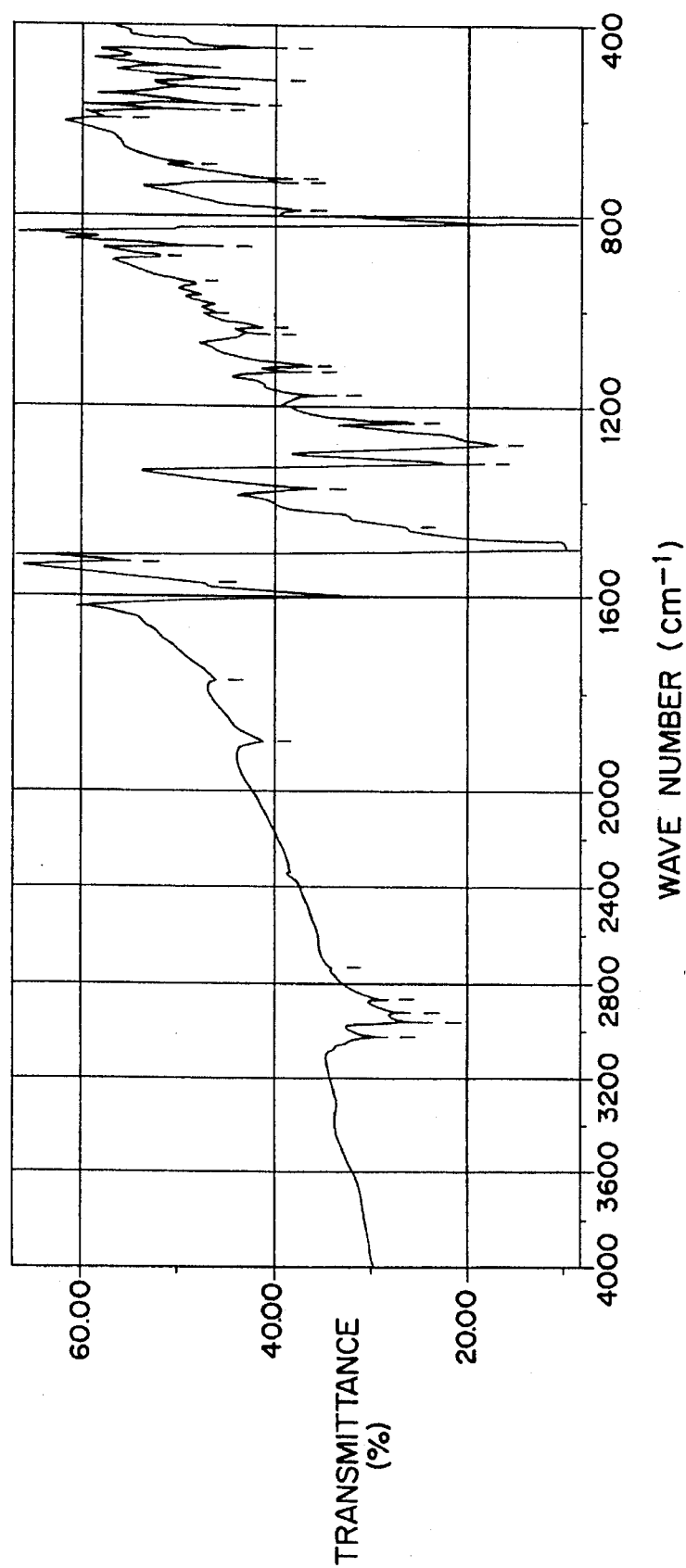

The results of the infrared spectroscopic analysis of the resulting product are shown in FIG. 4.

Elemental analysis (%) Calcd.: C, 89.17; H, 7.24; N, 3.59
Found: C, 88.98; H, 7.22; N, 3.78

Melting point: 204.4° C.

Synthesis Example 8

According to the same manner as that described in Synthesis Example 7 except for using 23.2 g of 3,4-dimethyliodobenzene in place of 2,4-dimethyliodobenzene to give N,N'-bis(3,4-dimethylphenyl)-N,N'-bis(4'-ethylbiphenyl-4

-yl)-3,3'-dimethylbenzidine of the above formula (1-h) (7.9 g, yield: 22.1%).

Figure 5:
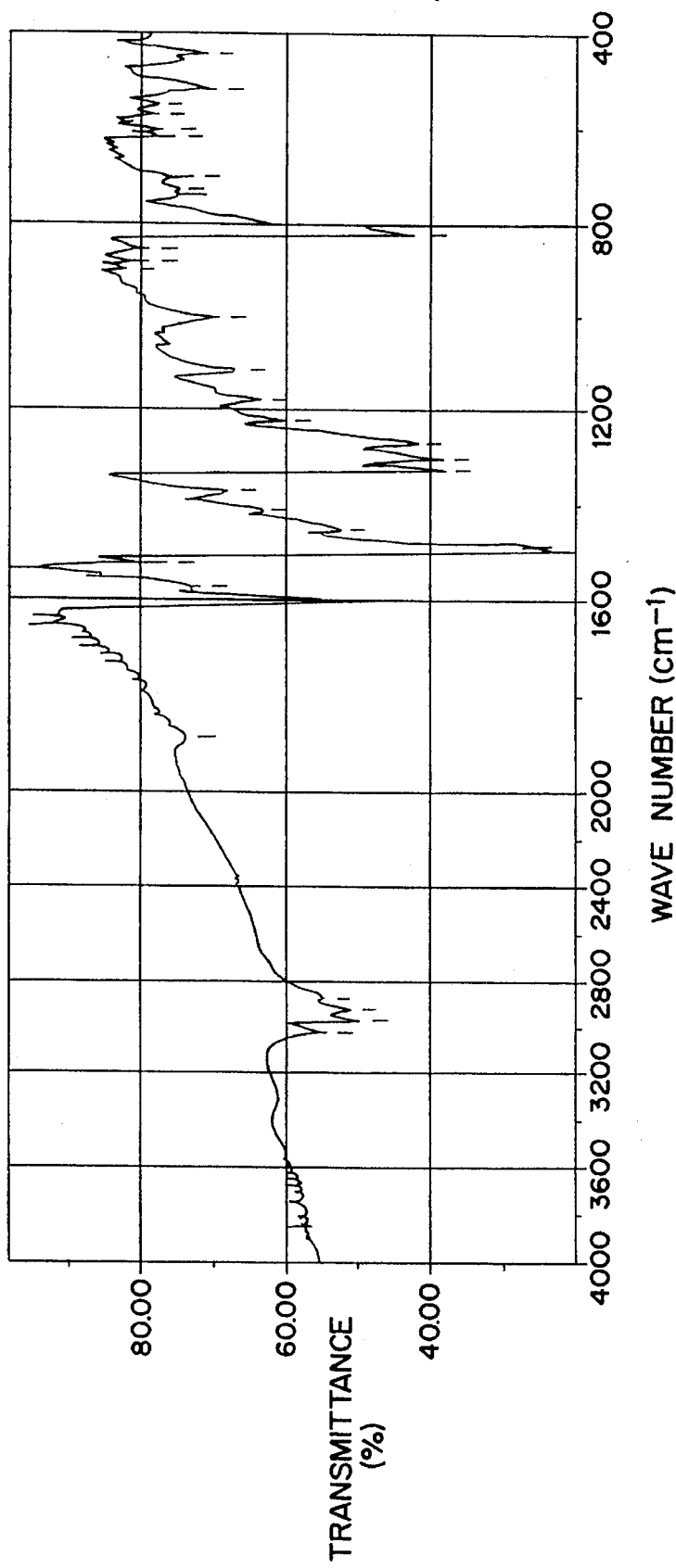

The results of the infrared spectroscopic analysis of the resulting product are shown in FIG. 5.

Elemental analysis (%), Calcd.: C, 89.17; H, 7.24; N, 3.59 Found: C, 88.94; H, 7.21; N, 3.83

Melting point: 236.3° C.

Synthesis Examples 9 and 10

According to the same manner as that described in Synthesis Example 7, compounds of the formulas (1-i) and (1-j) were obtained, respectively, using a suitable starting material.

Melting point of the compound of the formula (1-i): 218.4° C.

Melting point of the compound of the formula (1-j): 237.2° C.

Examples 1 to 10 and Comparative Examples 1 to 7 (Single-layer type electrophotosensitive material for digital light source)

5 Parts by weight of X-type metal-free phthalocyanine as the charge generating material, 50 parts by weight of a benzidine derivative as the hole transferring material (HTM), 30 parts by weight of 3,5-dimethyl-3',5'-di-tert-butyldiphenoquinone of the formula (12):

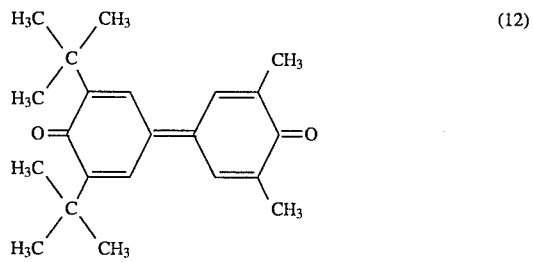
(12)

as the electron transferring material and 100 parts by weight of polycarbonate as the binding resin were mixed/dispersed with 800 parts by weight of tetrahydrofuran using a ball mill for 50 hours to prepare a coating solution for single-layer type photosensitive layer. Then, this coating solution was applied on an aluminum tube as the conductive substrate by a dip coating method, followed by hot-air drying at 100° C. for 60 minutes to give a single-layer type electrophotosensitive material for digital light source which has a single-layer type photosensitive layer of 15 to 20 μm in film thickness.

The respective compounds of the benzidine derivative used in Examples 1 to 10 are shown by the number of the compounds in Table 1. Further, the respective benzidine derivatives of the numbers (13) to (19) used in Comparative Examples 1 to 7 are the following compounds.

(13)

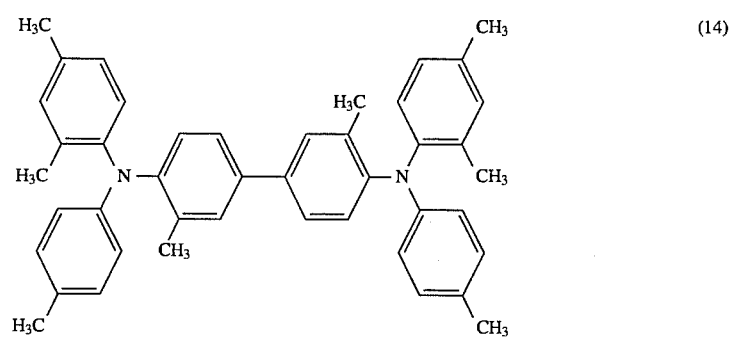
(14)

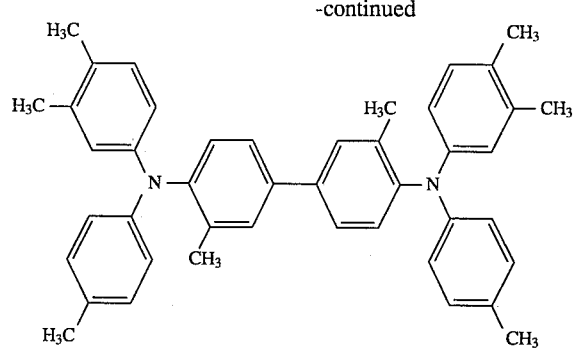
(15)
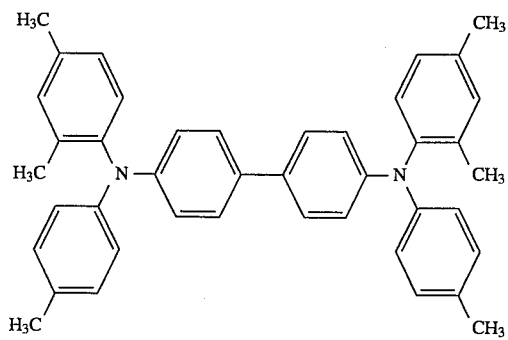
(16)
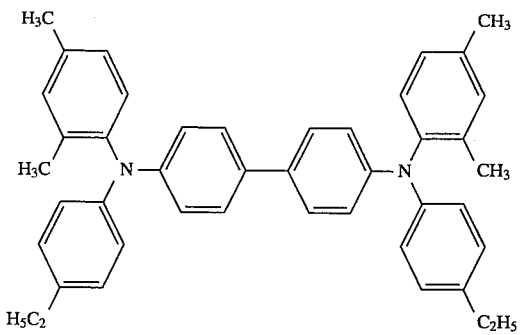
(17)
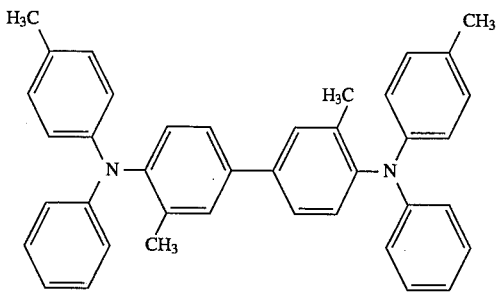
(18)

-continued

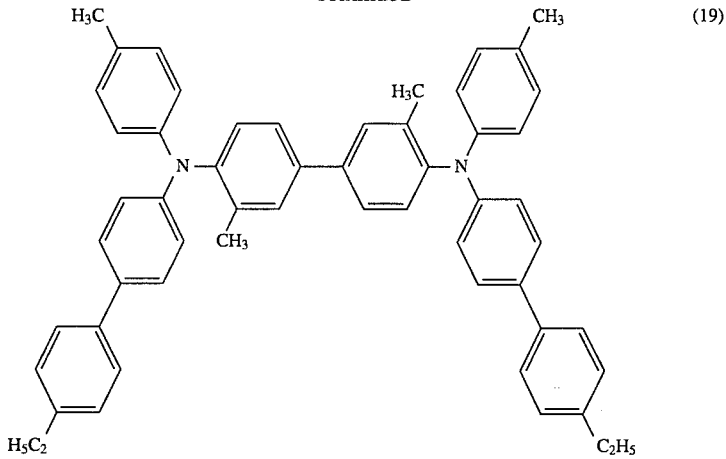

(19)

The melting point of benzidine derivatives (13) to (19) used in the respective Comparative Examples are shown below, respectively.

| (Number of compound) | (Melting point) |
| --- | --- |
| (13) | 171.0° C. |
| (14) | 195.2° C. |
| (15) | 201.2° C. |
| (16) | 194.3° C. |
| (17) | 193.5° C. |
| (18) | 170.1° C. |
| (19) | 135.6° C. |

The following tests were conducted as to the electrophotosensitive materials of the above Examples and Comparative Examples, and their characteristics were evaluated.

Initial electrical characteristics test (I)

By using a drum sensitivity tester manufactured by GENTEC Co., a voltage was applied on the surface of an electrophotosensitive material to charge the surface at +700 V. Then, monochromatic light having a wavelength of 780 nm (half-width: 20 nm) and a light intensity of 16 µW/cm$^2$ from white light of a halogen lamp as an exposure light source through a band-pass filter was irradiated on the surface of the electrophotosensitive material for 80 msec. (irradiation time) and the time which is necessary for the above surface potential to be reduced to half, i.e. +350 V was measured, thereby calculating a half-life exposure $E_{1/2}$ (µJ/cm$^2$). Further, a surface potential at the time at which 330 msec. has passed since the beginning of exposure was measured as a potential after exposure $V_L$ (V).

Measurement of glass transition temperature

A photosensitive layer (about 5 mg) was peeled off from an electrophotosensitive material and the photosensitive layer was placed in an exclusive aluminum pan, which was sealed to prepare a sample to be measured. Then, the measurement was conducted as to the sample under the following conditions using a differential scanning calorimeter (type DSC8230D, manufactured by Rigaku Denki Co., Ltd.). An extrapolation glass transition temperature (Tig) of the sample was determined from the measurement results according to a "method for measuring a transition temperature of a plastic" defined in JIS K 7121.

Atmospheric gas: air
Heating rate: 20° C./minute

High-temperature resistance test

An electrophotosensitive material was attached to an imaging unit of a facsimile for normal paper (type LDC-650, manufactured by Mita Industrial Co., Ltd.) and stored at an atmospheric temperature of 50° C. for 10 days at a state where a cleaning blade was always pressure-contacted on the surface of the electrophotosensitive material at a linear pressure of 1.5 g/mm. Then, a state of the surface of the photosensitive layer was measured with an utility surface profile-measuring apparatus (type SE-3H, manufactured by Kosaka Kenkyusho Co., Ltd.) and a maximum depth of the resulting dent was recorded. In the following tables, the description "<0.3 µm" in the column of the dent means that no dent was observed at all because the surface roughness of a normal electrophotosensitive material having no dent is about 0.5µ.

The results are shown in Table 1.

TABLE 1

| | HTM | $V_L$ (V) | $E_{1/2}$ (µJ/cm$^2$) | Tig (°C.) | Dent (µm) |
| --- | --- | --- | --- | --- | --- |
| Example 1 | 1-a | 177 | 0.71 | 73.2 | <0.3 |
| Example 2 | 1-b | 170 | 0.68 | 72.1 | <0.3 |
| Example 3 | 1-c | 174 | 0.71 | 72.4 | <0.3 |
| Example 4 | 1-d | 162 | 0.68 | 73.5 | <0.3 |
| Example 5 | 1-e | 164 | 0.69 | 72.9 | <0.3 |
| Example 6 | 1-f | 166 | 0.68 | 72.5 | <0.3 |
| Example 7 | 1-g | 175 | 0.71 | 74.4 | <0.3 |
| Example 8 | 1-h | 179 | 0.71 | 74.7 | <0.3 |
| Example 9 | 1-i | 182 | 0.73 | 75.0 | <0.3 |
| Example 10 | 1-j | 184 | 0.72 | 75.2 | <0.3 |
| Comp. Example 1 | (13) | 218 | 0.90 | 65.3 | 1.8 |
| Comp. Example 2 | (14) | 215 | 0.90 | 72.7 | <0.3 |
| Comp. Example 3 | (15) | 207 | 0.85 | 73.9 | <0.3 |
| Comp. Example 4 | (16) | 210 | 0.85 | 73.0 | <0.3 |
| Comp. Example 5 | (17) | 212 | 0.87 | 73.1 | <0.3 |
| Comp. Example 6 | (18) | 245 | 1.17 | 65.6 | 1.6 |
| Comp. Example 7 | (19) | 178 | 0.70 | 68.4 | 1.1 |

As apparent from Table 1, all of the electrophotosensitive materials of the respective Comparative Example using a conventional benzidine derivative were inferior in durability and heat resistance because their extrapolation glass transition temperature (Tig) was low and large dent was observed in the high-temperature resistance test.

To the contrary, all of the electrophotosensitive materials of the respective Examples were superior in durability and heat resistance because their extrapolation glass transition temperature (Tig) was high and no dent was observed in the high-temperature resistance test, as well as their small half-life exposure $E_{1/2}$ ($\mu J/cm^2$) and low potential after exposure $V_L$ (V).

Examples 11 to 40 and Comparative Examples 8 to 31 (Single-layer type electrophotosensitive material for analogue light source)

5 Parts by weight of any one of azo pigments represented by the formulas:

layer type photosensitive layer of 15 to 20 μm in film thickness.

The respective benzidine derivatives used in the above Examples and Comparative Examples are shown by the number of the compounds described above.

The following initial electrical characteristics test (II) was conducted as to the respective single-layer type electrophotosensitive materials thus obtained, and their characteristics were evaluated.

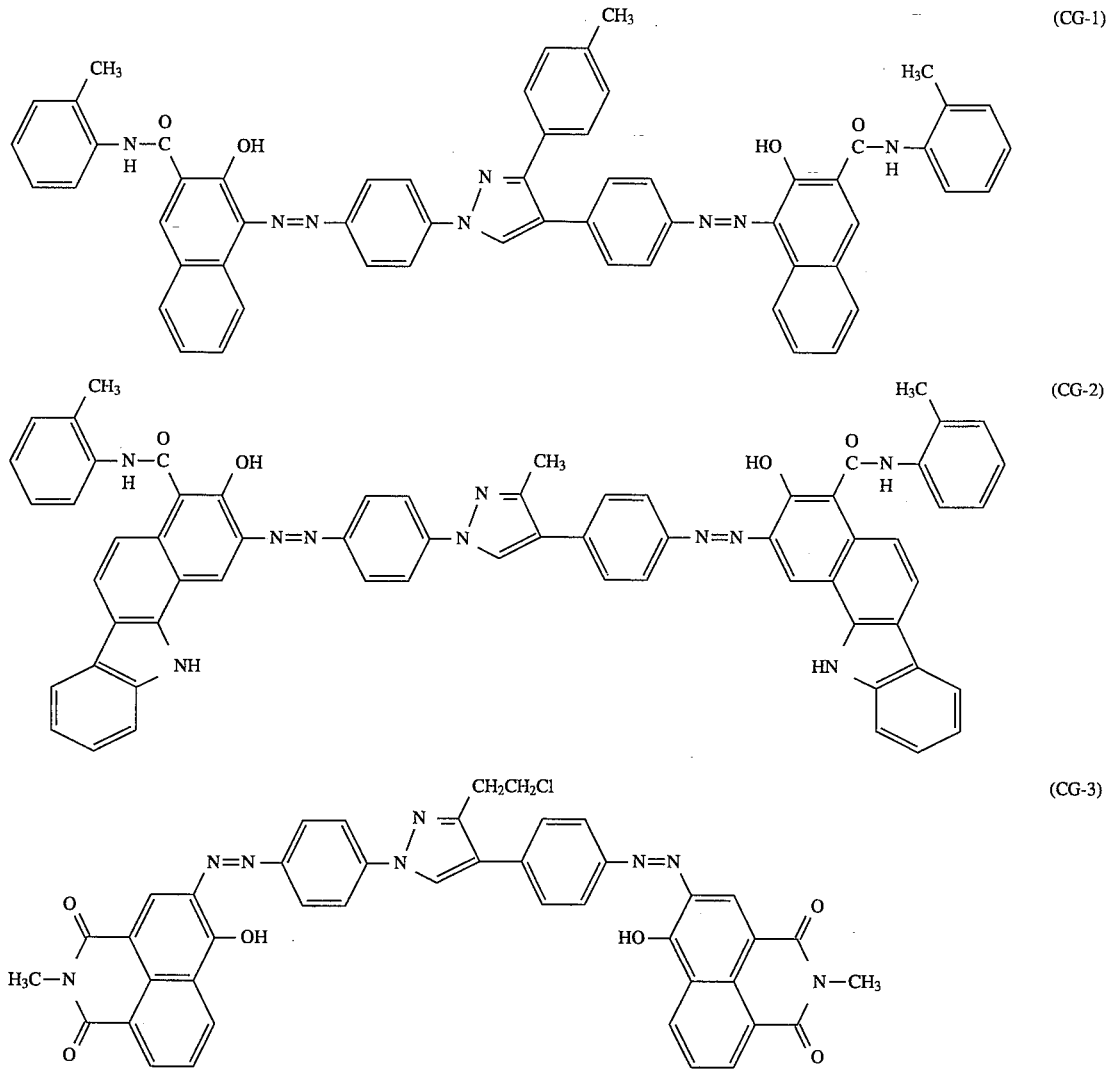

as the charge generating material (CGM), 70 parts by weight of a benzidine derivative as the hole transferring material (HTM), 20 parts by weight of 3,5-dimethyl-3',5'-di-tert-butyldiphenoquinone of the above formula (12) as the electron transferring material and 100 parts by weight of polycarbonate as the binding resin were mixed/dispersed with 800 parts by weight of tetrahydrofuran using a ball mill for 50 hours to prepare a coating solution for single-layer type photosensitive layer. Then, this coating solution was applied on an aluminum tube as the conductive substrate by a dip coating method, followed by hot-air drying at 100° C. for 60 minutes to give a single-layer type electrophotosensitive material for analogue light source which has a single- Initial electrical characteristics test (II)

By using a drum sensitivity tester manufactured by GENTEC Co., a voltage was applied on the surface of an electrophotosensitive material to charge the surface at +700 V. Then, white light (light intensity: 147 μW/cm²) of a halogen lamp as an exposure light was irradiated on the surface of the electrophotosensitive material for 50 msec. (irradiation time) and the time which is necessary for the above surface potential to be reduced to half, i.e. +350 V was measured, thereby calculating a half-life exposure $E_{1/2}$ (μJ/cm²). Further, a surface potential at the time at which 330 msec. has passed since the beginning of exposure was measured as a potential after exposure $V_L$ (V).

The above results are shown in Tables 2 to 4. In Table 4, the test results of glass transition temperature and high-temperature resistance measured according to the same manner as mentioned above are also shown.

TABLE 2

|  | HTM | CGM | $V_L$ (V) | $E_{1/2}$ ($\mu J/cm^2$) |
| --- | --- | --- | --- | --- |
| Example 11 | 1-a | CG-1 | 182 | 3.65 |
| Example 12 | 1-b | CG-1 | 179 | 3.60 |
| Example 13 | 1-c | CG-1 | 182 | 3.69 |
| Comp. Example 8 | (13) | CG-1 | 202 | 4.25 |
| Comp. Example 9 | (14) | CG-1 | 204 | 4.25 |
| Comp. Example 10 | (15) | CG-1 | 199 | 3.99 |
| Example 14 | 1-a | CG-2 | 184 | 3.69 |
| Example 15 | 1-b | CG-2 | 180 | 3.61 |
| Example 16 | 1-c | CG-2 | 181 | 3.59 |
| Comp. Example 11 | (13) | CG-2 | 210 | 4.32 |
| Comp. Example 12 | (14) | CG-2 | 213 | 4.33 |
| Comp. Example 13 | (15) | CG-2 | 207 | 4.40 |
| Example 17 | 1-a | CG-3 | 186 | 3.67 |
| Example 18 | 1-b | CG-3 | 182 | 3.64 |
| Example 19 | 1-c | CG-3 | 180 | 3.66 |
| Comp. Example 14 | (13) | CG-3 | 220 | 4.41 |
| Comp. Example 15 | (14) | CG-3 | 221 | 4.38 |
| Comp. Example 16 | (15) | CG-3 | 219 | 4.35 |

TABLE 3

|  | HTM | CGM | $V_L$ (V) | $E_{1/2}$ ($\mu J/cm^2$) |
| --- | --- | --- | --- | --- |
| Example 20 | 1-d | CG-1 | 182 | 3.69 |
| Example 21 | 1-e | CG-1 | 185 | 3.78 |
| Example 22 | 1-f | CG-1 | 184 | 3.74 |
| Comp. Example 8 | (13) | CG-1 | 202 | 4.25 |
| Comp. Example 17 | (16) | CG-1 | 206 | 4.27 |
| Comp. Example 18 | (14) | CG-1 | 204 | 4.25 |
| Comp. Example 19 | (17) | CG-1 | 209 | 4.30 |
| Example 23 | 1-d | CG-2 | 175 | 3.63 |
| Example 24 | 1-e | CG-2 | 179 | 3.69 |
| Example 25 | 1-f | CG-2 | 181 | 3.71 |
| Comp. Example 11 | (13) | CG-2 | 210 | 3.32 |
| Comp. Example 20 | (16) | CG-2 | 207 | 4.40 |
| Comp. Example 21 | (14) | CG-2 | 213 | 4.33 |
| Comp. Example 22 | (17) | CG-2 | 214 | 4.34 |
| Example 26 | 1-d | CG-3 | 183 | 3.70 |
| Example 27 | 1-e | CG-3 | 184 | 3.68 |
| Example 28 | 1-f | CG-3 | 180 | 3.69 |
| Comp. Example 14 | (13) | CG-3 | 220 | 4.41 |
| Comp. Example 23 | (16) | CG-3 | 219 | 4.35 |
| Comp. Example 24 | (14) | CG-3 | 221 | 4.38 |
| Comp. Example 25 | (17) | CG-3 | 220 | 4.39 |

TABLE 4

|  | HTM | CGM | $V_L$ (V) | $E_{1/2}$ ($\mu J/cm^2$) | Tig (°C.) | Dent ($\mu m$) |
| --- | --- | --- | --- | --- | --- | --- |
| Example 29 | 1-g | CG-1 | 150 | 3.22 | 71.4 | <0.3 |
| Example 30 | 1-h | CG-1 | 149 | 3.20 | 72.0 | <0.3 |
| Example 31 | 1-i | CG-1 | 157 | 3.30 | 71.3 | <0.3 |
| Example 32 | 1-j | CG-1 | 159 | 3.29 | 70.9 | <0.3 |
| Comp. Example 8 | (13) | CG-1 | 202 | 4.25 | —* | — |
| Comp. Example 26 | (18) | CG-1 | 237 | 5.63 | —* | — |
| Comp. Example 27 | (19) | CG-1 | 152 | 3.24 | 66.7 | 1.5 |
| Example 33 | 1-g | CG-2 | 158 | 3.30 | 70.9 | <0.3 |
| Example 34 | 1-h | CG-2 | 151 | 3.20 | 72.2 | <0.3 |
| Example 35 | 1-i | CG-2 | 155 | 3.22 | 71.8 | <0.3 |
| Example 36 | 1-j | CG-2 | 159 | 3.29 | 70.5 | <0.3 |
| Comp. Example 11 | (13) | CG-2 | 210 | 4.32 | —* | — |
| Comp. Example 28 | (18) | CG-2 | 240 | 5.63 | —* | — |
| Comp. Example 29 | (19) | CG-2 | 154 | 3.21 | 65.9 | 1.4 |
| Example 37 | 1-g | CG-3 | 160 | 3.33 | 72.0 | <0.3 |
| Example 38 | 1-h | CG-3 | 155 | 3.25 | 71.1 | <0.3 |
| Example 39 | 1-i | CG-3 | 152 | 3.21 | 70.7 | <0.3 |
| Example 40 | 1-j | CG-3 | 159 | 3.27 | 71.5 | <0.3 |
| Comp. Example 14 | (13) | CG-3 | 220 | 4.41 | —* | — |
| Comp. Example 30 | (18) | CG-3 | 239 | 5.64 | —* | — |
| Comp. Example 31 | (19) | CG-31 | 156 | 3.23 | 66.2 | 1.6 |

*Not measured.

As apparent from Tables 2 to 4, all of the electrophotosensitive materials of the Examples were superior in sensitivity because of their small half-life exposure $E_{1/2}$ ($\mu J/cm^2$) and low potential after exposure $V_L$ (V). From Table 4, it is recognized that all of the electrophotosensitive materials of the respective Examples were superior in durability and heat resistance because their extrapolation glass transition temperature (Tig) was high and no dent was observed in the high-temperature resistance test.

Examples 41 to 46 (Multi-layer type electrophotosensitive material for digital light source)

2 Parts by weight of X-type metal-free phthalocyanine as the charge generating material and 1 part of polyvinyl butyral as the binding resin were mixed/dispersed with 120 parts by weight of dichloromethane using a ball mill for 50 hours to prepare a coating solution for charge generating layer. Then, this coating solution was applied on an aluminum tube by a dip coating method, followed by hot-air drying at 100° C. for 60 minutes to form a charge generating layer of 0.5 μm in film thickness.

Then, 80 parts by weight of a benzidine derivative as the hole transferring material and 100 part of polycarbonate as the binding resin were mixed/dispersed with 800 parts by weight of benzene using a ball mill for 50 hours to prepare a coating solution for charge transferring layer. Then, this coating solution was applied on the above charge generating layer by a dip coating method, followed by hot-air drying at 90° C. for 60 minutes to form a charge transferring layer of 15 μm in film thickness, thereby producing a multi-layer type electrophotosensitive material for digital light source.

The following initial electrical characteristics test (III) was conducted as to the respective multi-layer type electrophotosensitive materials thus obtained, and their characteristics were evaluated.

Initial electrical charateristics test (III)

By using a drum sensitivity tester manufactured by GENTEC Co., a voltage was applied on the surface of the electrophotosensitive materials of the Examples to charge the surface at −700 V. Then, monochromatic light having a wavelength of 780 nm (half-width: 20 nm) and a light intensity of 16 μW/cm² from white light of a halogen lamp as an exposure light source through a band-pass filter was irradiated on the surface of the electrophotosensitive material for 50 msec. (irradiation time) and the time which is necessary for the above surface potential to be reduced to half, i.e. −350 V was measured, thereby calculating a half-life exposure $E_{1/2}$ (μJ/cm²). Further, a surface potential at the time at which 330 msec. has passed since the beginning of exposure was measured as a potential after exposure $V_L$ (V).

The results are shown in Table 5.

TABLE 5

| | HTM | $V_L$ (V) | $E_{1/2}$ (μJ/cm²) |
|---|---|---|---|
| Example 41 | 1-a | −129 | 0.59 |
| Example 42 | 1-b | −124 | 0.56 |
| Example 43 | 1-g | −127 | 0.58 |
| Example 44 | 1-h | −130 | 0.59 |
| Example 45 | 1-d | −122 | 0.51 |
| Example 46 | 1-e | −124 | 0.53 |

As is apparent from Table 5, all of the electrophotosensitive materials of the respective Examples were superior in sensitivity because of their small half-life exposure $E_{1/2}$ (μJ/cm²) and low potential after exposure $V_L$ (V).

Synthesis Example 11

10.6 G of 3,3'-dimethylbenzidine, 46.4 g of 2,4-dimethyliodobenzene, 27.6 g of potassium carbonate and 2 g of copper powder were added in 150 ml of nitrobenzene, and the mixture was refluxed with vigorous stirring while a nitrogen gas was bubbling into this reaction system for 24 hours. The water produced in the reaction was removed out of the reaction system by azeotropic distillation with nitrobenzene.

After the reaction solution was cooled, the inorganic substance was filtered off. Further, nitrobenzen was distilled off by steam distillation to give the residue, which was dissolved in cyclohexane and the solution was purified by subjecting to silica gel chromatography and cyclohexane was distilled off to give a white precipitation. Then, the white precipitation was recrystallized from n-hexane to give N,N,N',N'-tetrakis(2,4-dimethylphenyl)-3,3'-dimethylbenzidine of the above formula (2-a) (13.24 g, yield: 42.1%).

Figure 6:
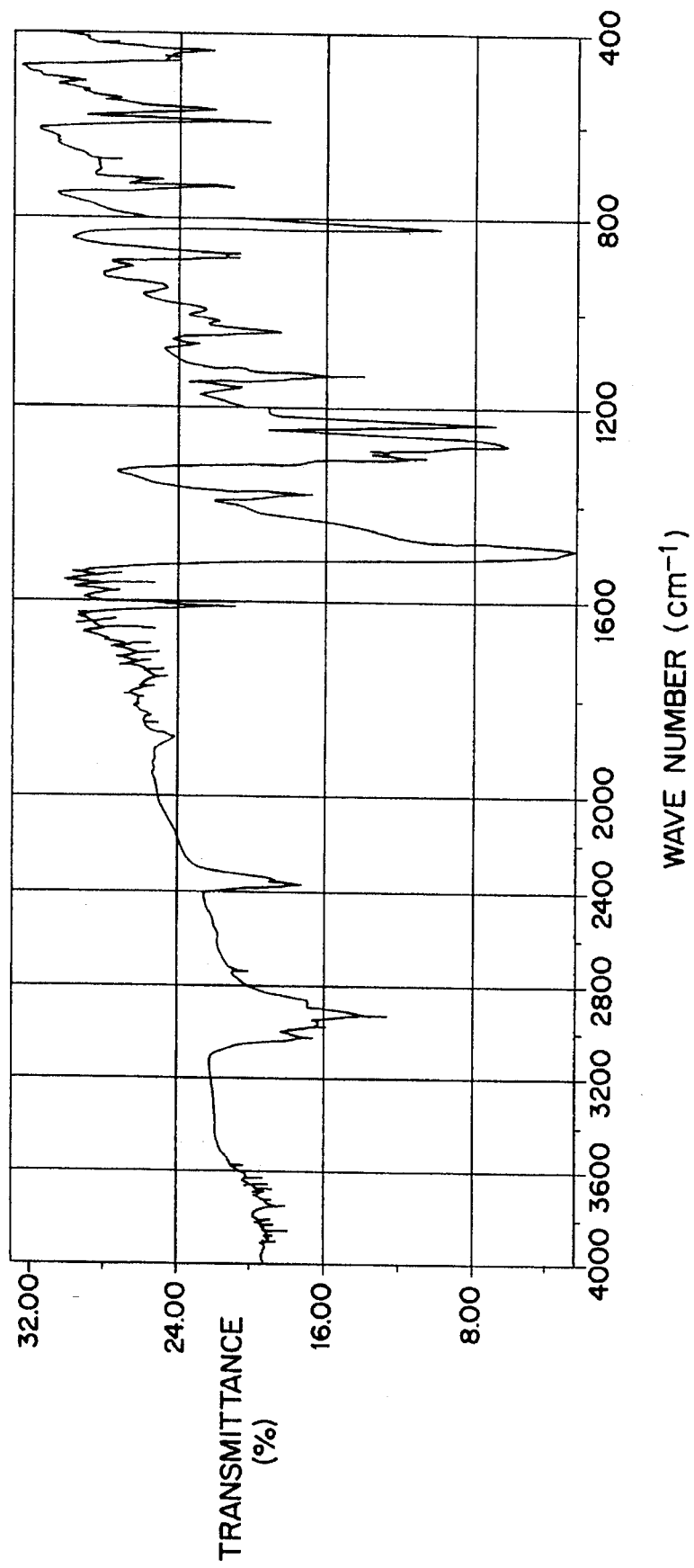

The results of the infrared spectroscopic analysis of the resulting product are shown in FIG. 6

Elemental analysis (%), Calcd.: C, 87.65; H, 7.69; N, 4.45 Found: C, 87.76; H, 7.81; N, 4.43

Melting point: 239.9° C.

Synthesis Examples 12 to 16

According to the same manner as that described in Synthesis Example 11, compounds of the formulas (2-b) to (2-f) were obtained, respectively, using a suitable starting material.

| (Number of compound) | (Melting point) |
|---|---|
| (2-b) | 210.3° C. |
| (2-c) | 201.4° C. |
| (2-d) | 217.8° C. |
| (2-e) | 210.0° C. |
| (2-f) | 199.2° C. |

Examples 47 to 49 and Comparative Examples 32 to 37

(Electrophotosensitive material for digital light source)

According to the same manner as that described in Example 1 except for using a benzidine derivative shown by the number of the compound in Table 6 as the hole transferring material (HTM), an electrophotosensitive material for digital light source which has a single-layer type photosensitive layer of 15 to 20 μm in film thickness was produced.

The benzidine derivatives of the numbers (20) to (25) used in Comparative Examples 32 to 37 are the following compounds.

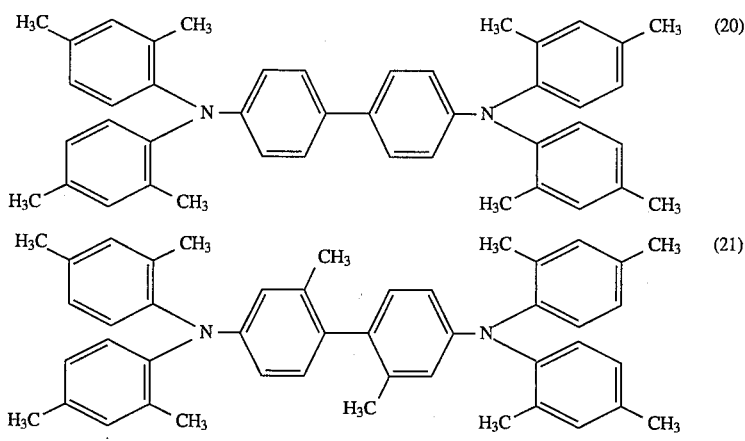

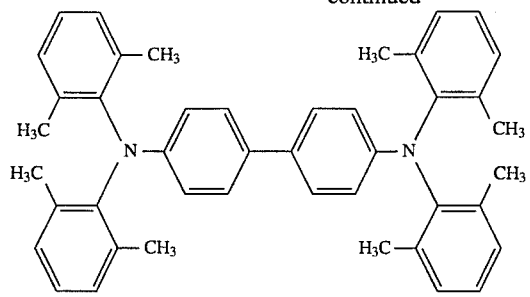
(22)

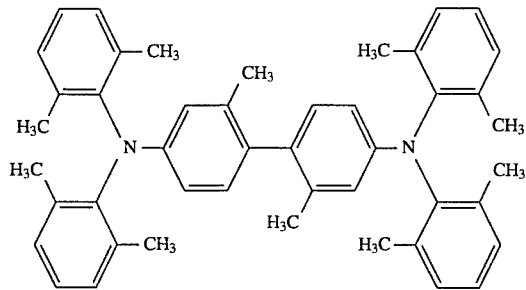
(23)

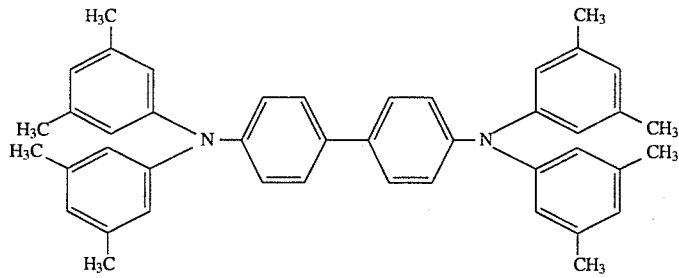
(24)

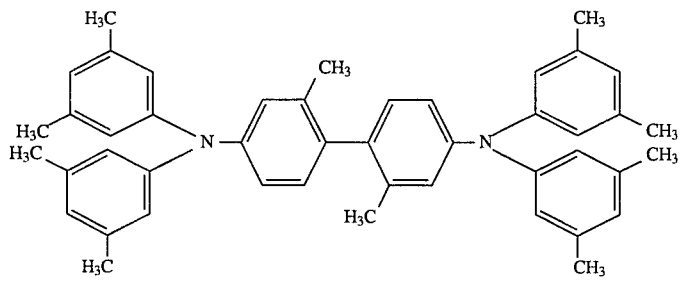
(25)

The melting point of benzidine derivatives (20) to (25) are shown below, respectively.

| (Number of compound) | (Melting point) |
|---|---|
| (20) | 220.1° C. |
| (21) | 219.7° C. |
| (22) | 204.2° C. |
| (23) | 195.9° C. |
| (24) | 203.3° C. |
| (25) | 201.0° C. |

According to the same manner as that described in Example 1, the resulting electrophotosensitive materials were subjected to the initial electrical characteristics test (I), the measurement of glass transition temperature and the high-temperature resistance test. The results are shown in Table 6.

TABLE 6

| | HTM | $V_L$ (V) | $E_{1/2}$ (μJ/cm$^2$) | Tig (°C.) | Dent (μm) |
|---|---|---|---|---|---|
| Example 47 | 2-a | 210 | 0.88 | 75.0 | <0.3 |
| Example 48 | 2-c | 215 | 0.90 | 72.7 | <0.3 |
| Example 49 | 2-d | 204 | 0.83 | 74.2 | <0.3 |
| Comp. Example 1 | (13) | 218 | 0.90 | 65.3 | 1.8 |
| Comp. Example 32 | (20) | 239 | 1.24 | 74.6 | <0.3 |
| Comp. Example 33 | (21) | 231 | 1.08 | 74.5 | <0.3 |
| Comp. Example 34 | (22) | 244 | 1.44 | 73.6 | <0.3 |
| Comp. Example 35 | (23) | 230 | 1.15 | 72.9 | <0.3 |
| Comp. Example 36 | (24) | 243 | 1.42 | 73.4 | <0.3 |
| Comp. Example 37 | (25) | 233 | 1.11 | 73.2 | <0.3 |

Examples 50 to 58 and Comparative Examples 38 to 55

(Electrophotosensitive material for analogue light source)

According to the same manner as that described in Example 11 except for using a benzidine derivative described in Tables 7 and 8 as the hole transferring material, a single-layer type electrophotosensitive material for analogue light source was produced. The resulting electrophotosensitive materials were subjected to the same initial electrical characteristics test (II) as that of Example 11, and their characteristics were evaluated. The results are shown in Tables 7 and 8.

TABLE 7

|  | HTM | CGM | $V_L$ (V) | $E_{1/2}$ (μJ/cm$^2$) |
|---|---|---|---|---|
| Example 50 | 2-a | CG-1 | 200 | 4.02 |
| Example 51 | 2-c | CG-1 | 204 | 4.25 |
| Example 52 | 2-d | CG-1 | 194 | 3.95 |
| Comp. Example 8 | (13) | CG-1 | 202 | 4.25 |
| Comp. Example 38 | (20) | CG-1 | 236 | 4.48 |
| Comp. Example 39 | (21) | CG-1 | 224 | 4.39 |
| Comp. Example 40 | (22) | CG-1 | 237 | 4.53 |
| Comp. Example 41 | (23) | CG-1 | 222 | 4.36 |
| Comp. Example 42 | (24) | CG-1 | 241 | 4.55 |
| Comp. Example 43 | (25) | CG-1 | 227 | 4.40 |
| Example 53 | 2-a | CG-2 | 201 | 4.03 |
| Example 54 | 2-c | CG-2 | 199 | 4.00 |
| Example 55 | 2-d | CG-2 | 197 | 3.98 |
| Comp. Example 11 | (13) | CG-2 | 210 | 4.32 |
| Comp. Example 44 | (20) | CG-2 | 245 | 4.58 |
| Comp. Example 45 | (21) | CG-2 | 239 | 4.50 |
| Comp. Example 46 | (22) | CG-2 | 238 | 4.47 |
| Comp. Example 47 | (23) | CG-2 | 230 | 4.45 |
| Comp. Example 48 | (24) | CG-2 | 249 | 4.61 |
| Comp. Example 49 | (25) | CG-2 | 232 | 4.52 |

TABLE 8

|  | HTM | CGM | $V_L$ (V) | $E_{1/2}$ (μJ/cm$^2$) |
|---|---|---|---|---|
| Example 56 | 2-a | CG-3 | 204 | 4.19 |
| Example 57 | 2-c | CG-3 | 206 | 4.24 |
| Example 58 | 2-d | CG-3 | 200 | 4.20 |
| Comp. Example 14 | (13) | CG-3 | 220 | 4.41 |
| Comp. Example 50 | (20) | CG-3 | 250 | 4.62 |
| Comp. Example 51 | (21) | CG-3 | 241 | 4.56 |
| Comp. Example 52 | (22) | CG-3 | 260 | 4.68 |
| Comp. Example 53 | (23) | CG-3 | 233 | 4.44 |
| Comp. Example 54 | (24) | CG-3 | 259 | 4.70 |
| Comp. Example 55 | (25) | CG-3 | 239 | 4.52 |

Synthesis Example 17

16.1 G of N,N'-diacetyl-3,3',5,5'-tetramethylbenzidine, 21.8 g of p-iodotoluene, 13.8 g of potassium carbonate and 1 g of copper powder were added in 150 ml of nitrobenzene, and the mixture was refluxed with vigorous stirring while a nitrogen gas was bubbling into this reaction system for 24 hours. The water produced in the reaction was removed out of the reaction system by azeotropic distillation with nitrobenzene.

After the reaction solution was cooled, the inorganic substance was filtered off. Further, nitrobenzen was distilled off by steam distillation to give the residue, which was dissolved in 100 ml of tetrahydrofuran together with 10% hydrochloric acid. The solution was deacetylated under reflux for 2 hours to give N,N'-di(4-methylphenyl)-3,3',5,5'-tetramethylbenzidine.

Then, 10.3 g of N,N'-di(4-methylphenyl)-3,3',5,5'-tetramethylbenzidine, 13.0 g of 4-tert-butyliodobenzene, 13.8 g of potassium carbonate and 1 g of copper powder were added in 150 ml of nitrobenzene, and the mixture was refluxed with vigorous stirring while a nitrogen gas was blowing into this reaction system for 24 hours. The water content produced in the reaction was removed out of the reaction system by azeotropic distillation with nitrobenzene, similar to the above case.

After the reaction solution was cooled, the inorganic substance was filtered off. Further, nitrobenzen was distilled off by steam distillation to give the residue, which was dissolved in cyclohexane and the solution was purified by subjecting to silica gel chromatography and cyclohexane was distilled off to give a white precipitation. Then, the white precipitation was recrystallized from n-hexane to give N,N'-di(4-methylphenyl)-N,N'-di(4-tert-butylphenyl)-3,3',5,5'-tetramethylbenzidine of the above formula (3-b) as an objective product (6.71 g, yield: 39.2%).

Figure 7:
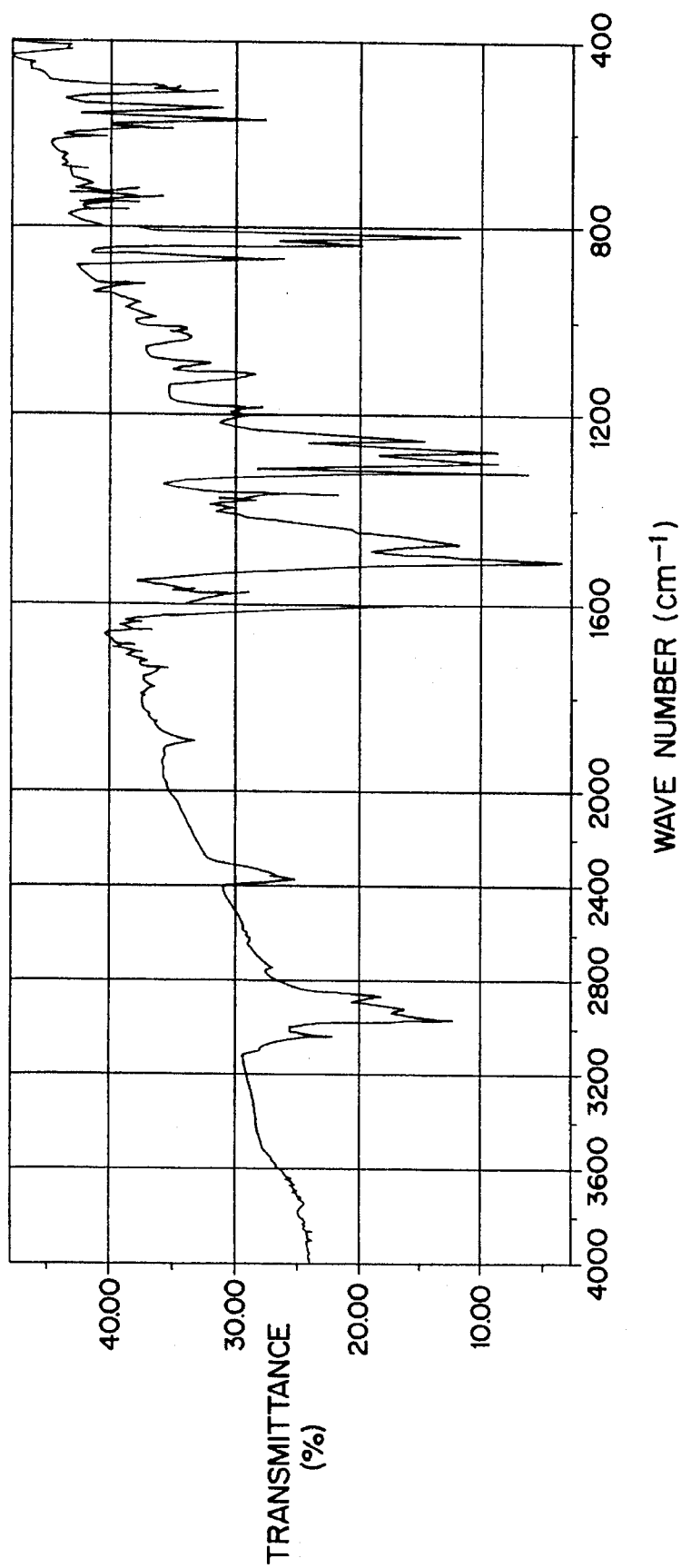

The results of the infrared spectroscopic analysis of the resulting product are shown in FIG. 7.

Elemental analysis (%), Calcd.: C, 87.67; H, 8.24; N, 4.09
Found: C, 87.60; H, 8.20; N, 4.20

Melting point: 276.0° C.

Synthesis Example 18

According to the same manner as that described in Synthesis Example 17 except for using the same molar amount of 4-methyliodobenzene in place of p-iodotoluene and using the same molar amount of 4-ethyl-4'-iodobiphenyl in place of 4-tert-butyliodobenzene, N,N'-bis(4-methylphenyl)-N,N'-bis(4'-ethylbiphenyl-4-yl)-3,5,3',5'-tetramethylbenzidine of the above formula (3-e) was obtained (9.2 g, yield:25.0%).

Figure 8:
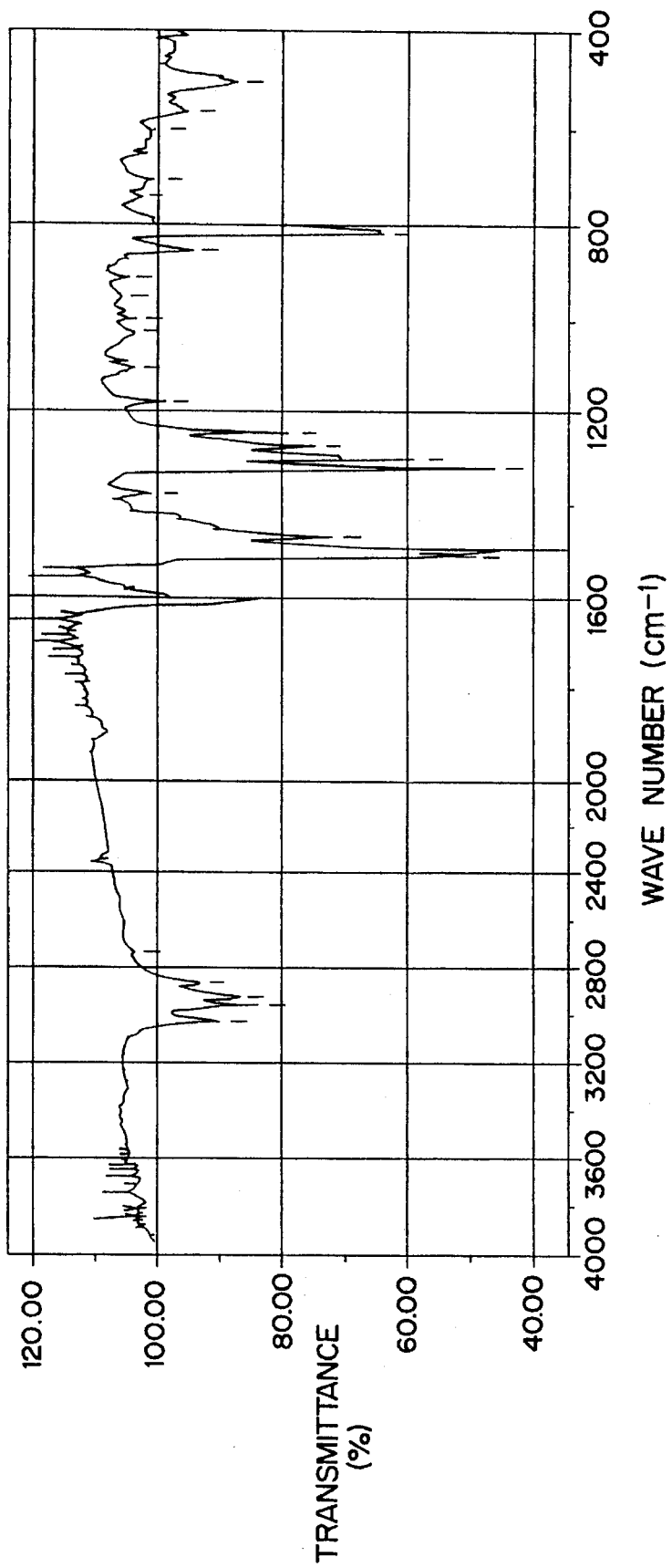

The results of the infrared spectroscopic analysis of the resulting product are shown in FIG. 8.

Elemental analysis (%), Calcd.: C, 89.17; H, 7.24; N, 3.59
Found: C, 89.10; H, 7.19; N, 3.61

Melting point: 181.6° C.

Synthesis Examples 19 to 22

According to the same manner as that described in Synthesis Example 17, benzidine derivatives of the formulas (3-a), (3-c), (3-d) and (3-f) were obtained, respectively, using a suitable starting material.

| (Number of compound) | (Melting point) |
|---|---|
| (3-a) | 280.5° C. |
| (3-c) | 277.3° C. |
| (3-d) | 198.7° C. |
| (3-f) | 200.7° C. |

Examples 59 to 64 and Comparative Examples 56 to 57

(Single-layer type electrophotosensitive material for digital light source)

According to the same manner as that described in Example 1 except for using a benzidine derivative described in Table 9 as the hole transferring material (HTM), an electrophotosensitive material having a single-layer type photosensitive layer of 15 to 20 μm in film thickness.

The benzidine derivatives used in the Examples were shown by the number of the compound in Table 9. Further, benzidine derivatives (26) to (27) used in Comparative Examples 56 to 57 are the following compounds.

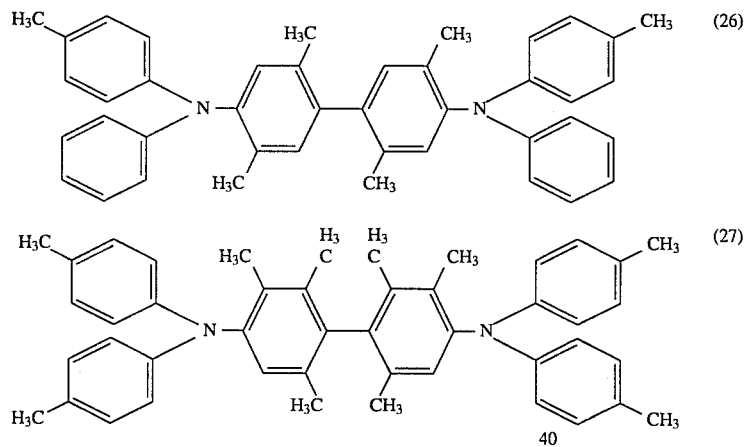

The melting point of benzidine derivatives (26) to (27) are shown below, respectively.

| (Number of compound) | (Melting point) |
|---|---|
| (26) | 224.1° C. |
| (27) | 301.5° C. |

According to the same manner as that described in Example 1, the resulting electrophotosensitive materials of the respective Examples and Comparative Examples were subjected to the initial electrical characteristics test (I), the measurement of glass transition temperature and the high-temperature resistance test. The results are shown in Table 9. Further, the test results of electrophotosensitive materials using benzidine derivatives (13) and (18) are also shown, for comparison.

TABLE 9

| | HTM | $V_L$ (V) | $E_{1/2}$ (μJ/cm$^2$) | Tig (°C.) | Dent (μm) |
|---|---|---|---|---|---|
| Example 59 | 3-a | 200 | 0.84 | 74.2 | <0.3 |
| Example 60 | 3-b | 190 | 0.79 | 73.4 | <0.3 |
| Example 61 | 3-c | 189 | 0.80 | 72.9 | <0.3 |
| Example 62 | 3-d | 181 | 0.73 | 77.4 | <0.3 |

TABLE 9-continued

| | HTM | $V_L$ (V) | $E_{1/2}$ (μJ/cm$^2$) | Tig (°C.) | Dent (μm) |
|---|---|---|---|---|---|
| Example 63 | 3-e | 180 | 0.72 | 77.3 | <0.3 |
| Example 64 | 3-f | 183 | 0.73 | 77.6 | <0.3 |
| Comp. Example 56 | (26) | 226 | 0.99 | 74.1 | <0.3 |
| Comp. Example 57 | (27) | —* | — | — | — |
| Comp. Example 1 | (13) | 218 | 0.90 | 65.3 | 1.8 |
| Comp. Example 6 | (18) | 245 | 1.17 | 65.6 | 1.6 |

*It was impossible to conduct measurement due to crystallization.

Examples 65 to 82 and Comparative Examples 58 to 63

(Electrophotosensitive material for analogue light source)

According to the same manner as that described in Example 11 except for using a benzidine derivative described in Tables 10 and 11 as the hole transferring material (HTM), a single-layer type electrophotosensitive material for analogue light source was produced. The resulting electrophotosensitive materials of the respective Examples and Comparative Examples were subjected to the same initial electrical characteristics test (II) as that of Example 11, and their characteristics were evaluated. The results are shown in Tables 10 and 11. Further, the test results of electrophotosensitive materials using benzidine derivatives (13) and (18) are also shown, for comparison.

TABLE 10

| | HTM | CGM | $V_L$ (V) | $E_{1/2}$ (μJ/cm$^2$) |
|---|---|---|---|---|
| Example 65 | 3-a | CG-1 | 193 | 4.03 |
| Example 66 | 3-b | CG-1 | 190 | 3.87 |
| Example 67 | 3-c | CG-1 | 191 | 3.98 |
| Comp. Example 58 | (26) | CG-1 | 217 | 4.51 |
| Comp. Example 59 | (27) | CG-1 | —* | — |
| Comp. Example 8 | (13) | CG-1 | 202 | 4.25 |
| Example 68 | 3-a | CG-2 | 196 | 4.06 |
| Example 69 | 3-b | CG-2 | 192 | 3.88 |
| Example 70 | 3-c | CG-2 | 189 | 3.86 |
| Comp. Example 60 | (26) | CG-2 | 218 | 4.50 |
| Comp. | (27) | CG-2 | —* | — |

TABLE 10-continued

|  | HTM | CGM | $V_L$ (V) | $E_{1/2}$ ($\mu$J/cm$^2$) |
| --- | --- | --- | --- | --- |
| Example 61 |  |  |  |  |
| Comp. Example 11 | (13) | CG-2 | 210 | 4.32 |
| Example 71 | 3-a | CG-3 | 192 | 4.02 |
| Example 72 | 3-b | CG-3 | 190 | 3.89 |
| Example 73 | 3-c | CG-3 | 195 | 3.90 |
| Comp. Example 62 | (26) | CG-3 | 216 | 4.52 |
| Comp. Example 63 | (27) | CG-3 | —* | — |
| Comp. Example 14 | (13) | CG-3 | 220 | 4.41 |

*It was imposible to conduct measurement due to crystallization.

TABLE 11

|  | HTM | CGM | $V_L$ (V) | $E_{1/2}$ ($\mu$J/cm$^2$) |
| --- | --- | --- | --- | --- |
| Example 74 | 3-d | CG-1 | 179 | 3.62 |
| Example 76 | 3-f | CG-1 | 180 | 3.65 |
| Comp. Example 8 | (13) | CG-1 | 202 | 4.25 |
| Comp. Example 26 | (18) | CG-1 | 237 | 5.63 |
| Example 77 | 3-d | CG-2 | 172 | 3.59 |
| Example 78 | 3-e | CG-2 | 175 | 3.61 |
| Example 79 | 3-f | CG-2 | 174 | 3.63 |
| Comp. Example 11 | (13) | CG-2 | 210 | 4.32 |
| Comp. Example 28 | (18) | CG-2 | 240 | 5.63 |
| Example 80 | 3-d | CG-3 | 180 | 3.61 |
| Example 81 | 3-e | CG-3 | 179 | 3.64 |
| Example 82 | 3-f | CG-3 | 182 | 3.67 |
| Comp. Example 14 | (13) | CG-3 | 220 | 4.41 |
| Comp. Example 30 | (18) | CG-3 | 239 | 5.64 |

Examples 83 and 84

(Multi-layer type electrophotosensitive material for digital light source)

According to the same manner as that described in Example 41 except for using those shown in Table 12 as the hole transferring material (HTM), a multi-layer type electrophotosensitive material for digital light source was produced.

According to the same manner as that described in Example 11, the resulting electrophotosensitive materials were subjected to the initial electrical characteristics test (II), and their characteristics were evaluated. The test results are shown in Table 12.

TABLE 12

|  | HTM | $V_L$ (V) | $E_{1/2}$ ($\mu$J/cm$^2$) |
| --- | --- | --- | --- |
| Example 83 | 3-d | −138 | 0.61 |
| Example 84 | 3-e | −135 | 0.62 |

Synthesis Example 23

According to the same manner as that described in Synthesis Example 1, 16.19 of N,N'-diacetyl-2,5,2',5'-tetramethylbenzidine was reacted with 21.8 g of 4-methyliodobenzene to give N,N'-bis(4-methylphenyl)-2,5,2',5'-tetramethylbenzidine. Further, 12.0 g of N,N'-bis(4-methylphenyl)-2,5,2',5'-tetramethylbenzidine was reacted with 13.0 g of 4-tert-butyliodobenzene according to the same manner as that described in Synthesis Example 1 to give N,N'-bis(4 -methylphenyl)-N,N'-bis(4-tert-butylphenyl)-2,5,2',5'-tetramethylbenzidine of the formula (4-a) (9.0 g, yield: 27.1%).

Figure 9:
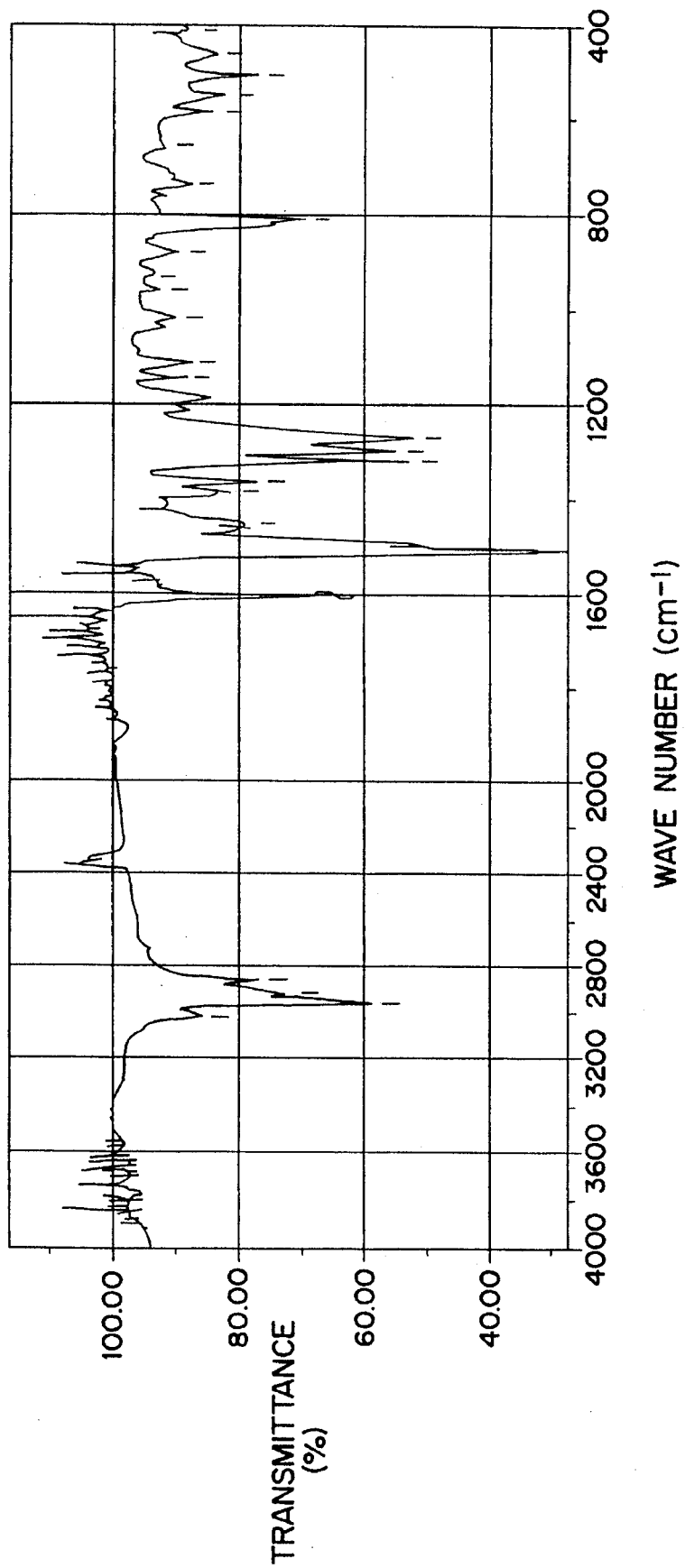

The results of the infrared spectroscopic analysis of the resulting product are shown in FIG. 9.

Elemental analysis (%), Calcd.: C, 87.65; H, 8.26; N, 4.09 Found: C, 87.61; H, 8.19; N, 4.19

Melting point: 180.9° C.

Synthesis Example 24

According to the same manner as that described in Synthesis Example 23, a benzidine derivative of the formula (4-b) was obtained using a suitable starting material.

Melting point: 191.5° C.

Examples 85 and 86

(Single-layer type electrophotosensitive material for digital light source)

According to the same manner as that described in Example 1 except for using a benzidine derivative shown by the number of the compound in Table 13 as the hole transferring material (HTM), a single-layer type electrophotosensitive material for digital light source was obtained.

The resulting single-layer type electrophotosensitive materials were subjected to the initial electrical characteristics test (I), the measurement of the glass transition temperature and the high-temperature resistance test, and their characteristics were evaluated. The results are shown in Table 13. Further, the test results of electrophotosensitive materials using benzidine derivatives (13), (18) and (26) as the Comparative Example are also shown.

TABLE 13

|  | HTM | $V_L$ (V) | $E_{1/2}$ ($\mu$J/cm$^2$) | Tig (°C.) | Dent ($\mu$m) |
| --- | --- | --- | --- | --- | --- |
| Example 85 | 4-a | 181 | 0.73 | 73.3 | <0.3 |
| Example 86 | 4-b | 179 | 0.71 | 73.5 | <0.3 |
| Comp. Example 1 | (13) | 218 | 0.90 | 65.3 | 1.8 |
| Comp. Example 6 | (18) | 245 | 1.17 | 65.6 | 1.6 |
| Comp. Example 56 | (26) | 226 | 0.99 | 74.1 | <0.3 |

Examples 87 to 92

(Electrophotosensitive material for analogue light source)

According to the same manner as that described in Example 11 except for using a benzidine derivative shown in Table 14 as the hole transferring material (HTM), a single-layer type electrophotosensitive material for analogue light source was produced. The resulting single-layer type electrophotosensitive materials of the respective Examples and Comparative Examples were subjected to the same initial electrical characteristics test (II) as that of Example 11, and their characteristics were evaluated. The results are shown in Table 14. Further, the test results of electrophotosensitive materials using benzidine derivatives (13), (18) and (26) as the hole transferring material are also shown, for comparison.

TABLE 14

| | HTM | CGM | $V_L$ (V) | $E_{1/2}$ ($\mu J/cm^2$) |
|---|---|---|---|---|
| Example 87 | 4-a | CG-1 | 178 | 3.65 |
| Example 88 | 4-b | CG-1 | 177 | 3.64 |
| Comp. Example 8 | (13) | CG-1 | 202 | 4.25 |
| Comp. Example 26 | (18) | CG-1 | 237 | 5.63 |
| Comp. Example 58 | (26) | CG-1 | 217 | 4.51 |
| Example 89 | 4-a | CG-2 | 175 | 3.63 |
| Example 90 | 4-b | CG-2 | 176 | 3.66 |
| Comp. Example 11 | (13) | CG-2 | 210 | 4.32 |
| Comp. Example 28 | (18) | CG-2 | 240 | 5.63 |
| Comp. Example 60 | (26) | CG-2 | 218 | 4.50 |
| Example 91 | 4-a | CG-3 | 179 | 3.69 |
| Example 92 | 4-b | CG-3 | 182 | 3.69 |
| Comp. Example 14 | (13) | CG-3 | 220 | 4.41 |
| Comp. Example 30 | (18) | CG-3 | 239 | 5.64 |
| Comp. Example 62 | (26) | CG-3 | 216 | 4.52 |

Examples 93 and 94

(Multi-layer type electrophotosensitive material for digital light source)

According to the same manner as that described in Example 41 except for using those shown in Table 15 as the hole transferring material (HTM), a multi-layer type electrophotosensitive material for digital light source was produced.

The resulting multi-layer type electrophotosensitive materials were subjected to the initial electrical characteristics test (III) according to the same manner as that described in Example 41, and their characteristics were evaluated. The results are shown in Table 15.

TABLE 15

| | HTM | $V_L$ (V) | $E_{1/2}$ ($\mu J/cm^2$) |
|---|---|---|---|
| Example 93 | 4-a | −136 | 0.63 |
| Example 94 | 4-b | −133 | 0.60 |

Synthesis Example 25

10.6 G of 3,3'-dimethylbenzidine, 33.9 g of 4-ethyl-4'-iodobiphenyl, 27.6 g of potassium carbonate and 2 g of copper powder were added in 150 ml of nitrobenzene, and the mixture was refluxed with vigorous stirring while a nitrogen gas was bubbling into this reaction system for 24 hours. The water produced in the reaction was removed out of the reaction system by azeotropic distillation with nitrobenzene.

After the reaction solution was cooled, the inorganic substance was filtered off. Further, nitrobenzen was distilled off by steam distillation to give the residue, which was dissolved in cyclohexane and the solution was purified by subjecting to silica gel chromatography and cyclohexane was distilled off to give a white precipitation. Then, the white precipitation was recrystallized from n-hexane to give N,N, N',N'-tetrakis(4'-ethylbiphenyl-4-yl)-3,3'-dimethylbenzidine of the above formula (5-b) (14.7 g, yield: 31.5%).

Figure 10:
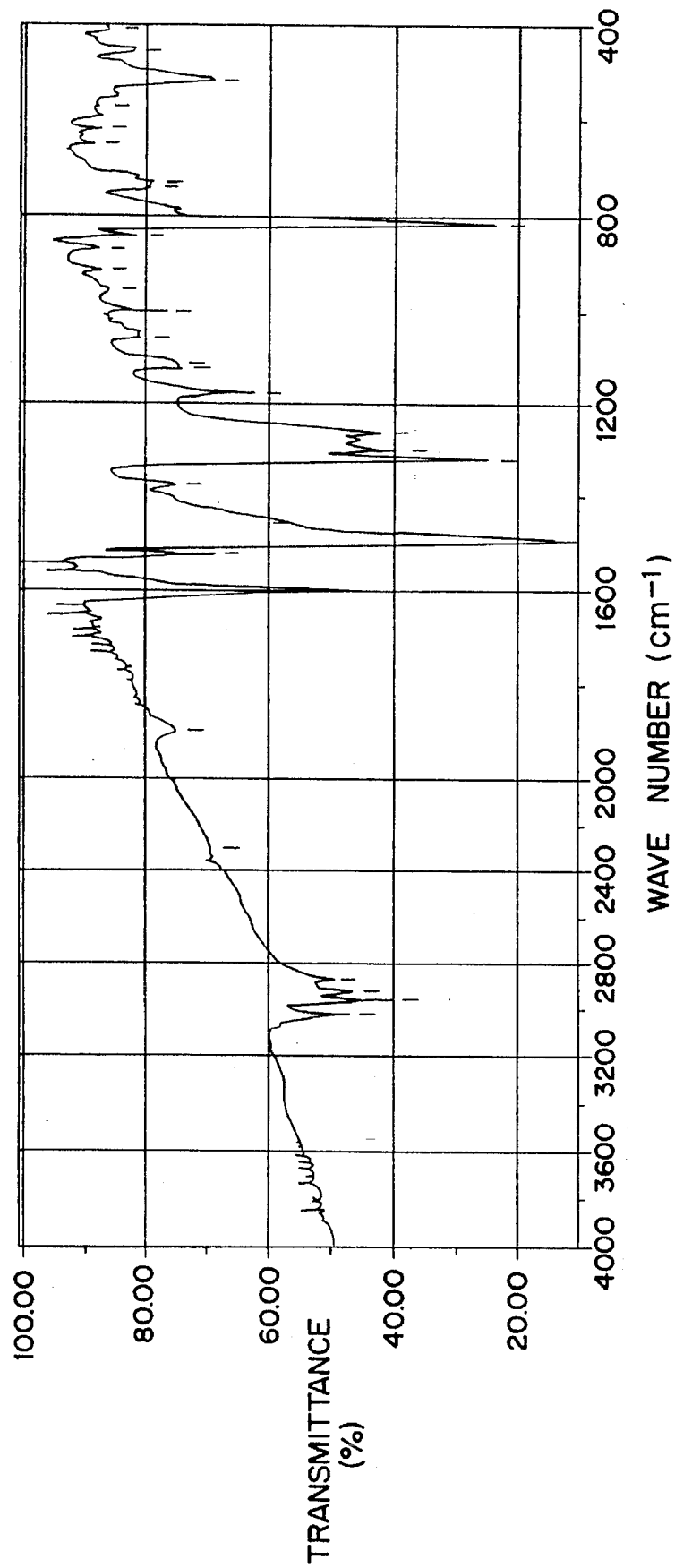

The results of the infrared spectroscopic analysis of the resulting product are shown in FIG. 10

Elemental analysis (%), Calcd.: C, 90.07; H, 6.93; N, 3.00
Found: C, 89.98; H, 6.91; N, 3.01
Melting point: 270.4° C.

Synthesis Examples 26 and 27

According to the same manner as that described in Synthesis Example 25, benzidine derivatives of the formulas (5-a) and (5-c) were obtained using a suitable starting material.

| (Number of compound) | (Melting point) |
|---|---|
| (5-a) | 203.3° C. |
| (5-c) | 281.3° C. |

Examples 95 to 97

(Single-layer type electrophotosensitive material for digital light source)

According to the same manner as that described in Example 1 except for using a benzidine derivative shown by the number of the compound in Table 16 as the hole transferring material (HTM), a single-layer type electrophotosensitive material for digital light source was produced. The resulting electrophotosensitive materials of the above Examples and Comparative Examples were subjected to the initial electrical characteristics test (II), the measurement of the glass transition temperature and the high-temperature resistance test, and their characteristics were evaluated. The results are shown in Table 16. Further, the test results of electrophotosensitive materials using benzidine derivatives of the formulas (13), (18) and (19) are also shown, for comparison.

TABLE 16

| | HTM | $V_L$ (V) | $E_{1/2}$ ($\mu J/cm^2$) | Tig (°C.) | Dent ($\mu m$) |
|---|---|---|---|---|---|
| Example 95 | 5-a | 171 | 0.70 | 76.1 | <0.3 |
| Example 96 | 5-b | 164 | 0.65 | 75.2 | <0.3 |
| Example 97 | 5-c | 174 | 0.69 | 76.2 | <0.3 |
| Comp. Example 1 | (13) | 218 | 0.90 | 65.3 | 1.8 |
| Comp. Example 6 | (18) | 245 | 1.17 | 65.6 | 1.6 |
| Comp. Example 7 | (19) | 178 | 0.70 | 68.4 | 1.1 |

Examples 98 to 106

(Electrophotosensitive material for analogue light source)

According to the same manner as that described in Example 11 except for using a benzidine derivative described in Table 17 as the hole transferring material (HTM), a single-layer type electrophotosensitive material for analogue light source was produced. The resulting electrophotosensitive materials of the respective Examples and Comparative Examples were subjected to the same initial electrical characteristics test (II) as that of Example 11, and their characteristics were evaluated. The test results are shown in Table 17. Further, the test results of electrophotosensitive materials using benzidine derivatives of the formulas (13), (18) and (19) are also shown, for comparison.

TABLE 17

|  | HTM | CGM | $V_L$ (V) | $E_{1/2}$ (μJ/cm²) |
|---|---|---|---|---|
| Example 98 | 5-a | CG-1 | 151 | 3.21 |
| Example 99 | 5-b | CG-1 | 146 | 3.17 |
| Example 100 | 5-c | CG-1 | 154 | 3.29 |
| Comp. Example 8 | (13) | CG-1 | 202 | 4.25 |
| Comp. EXAMPLE 26 | (18) | CG-1 | 237 | 5.63 |
| Comp. Example 27 | (19) | CG-1 | 152 | 3.24 |
| Example 101 | 5-a | CG-2 | 150 | 3.20 |
| Example 102 | 5-b | CG-2 | 149 | 3.19 |
| Example 103 | 5-c | CG-2 | 152 | 3.29 |
| Comp. Example 11 | (13) | CG-2 | 210 | 4.32 |
| Comp. Example 28 | (18) | CG-2 | 240 | 5.63 |
| Comp. Example 29 | (19) | CG-2 | 154 | 3.21 |
| Example 104 | 5-a | CG-3 | 148 | 3.21 |
| Example 105 | 5-b | CG-3 | 151 | 3.31 |
| Example 106 | 5-c | CG-3 | 153 | 3.20 |
| Comp. Example 14 | (13) | CG-3 | 220 | 4.41 |
| Comp. Example 30 | (18) | CG-3 | 239 | 5.64 |
| Comp. Example 31 | (19) | CG-3 | 156 | 3.23 |

Examples 107 and 108

(Multi-layer type electrophotosensitive material for digital light source)

According to the same manner as that described in Example 41 except for using those shown in Table 18 as the hole transferring material (HTM), a multi-layer type electrophotosensitive material for digital light source was produced.

The resulting multi-layer type electrophotosensitive materials were subjected to the initial electrical characteristics test (III) according to the same manner as that described in Example 41, and their characteristics were evaluated. The test results are shown in Table 18.

TABLE 18

|  | HTM | $V_L$ (V) | $E_{1/2}$ (μJ/cm²) |
|---|---|---|---|
| Example 107 | 5-a | −120 | 0.51 |
| Example 108 | 5-b | −124 | 0.53 |

Synthesis Example 28

According to the same manner as that described in Synthesis Example 1, 14.9 g of N,N'-diacetyl-3,3'-dimethylbenzidine was reacted with 21.8 g of para-iodobenzene to give N,N'-di-p-tolyl-3,3'-dimethylbenzidine. Further, 12.0 g of N,N'-di-p-tolyl-3,3'-dimethylbenzidine was reacted with 15.4 g of 4-ethyl-4'-iodobiphenyl according to the same manner as that described in Synthesis Example 1 to give N,N'-di-p-tolyl-N,N'-di(4'-ethylbiphenyl-4-yl)-3,3'-dimethylbenzidine (hereinafter referred to as 6-c) (8.82 g, yield: 23.7%).

Figure 11:
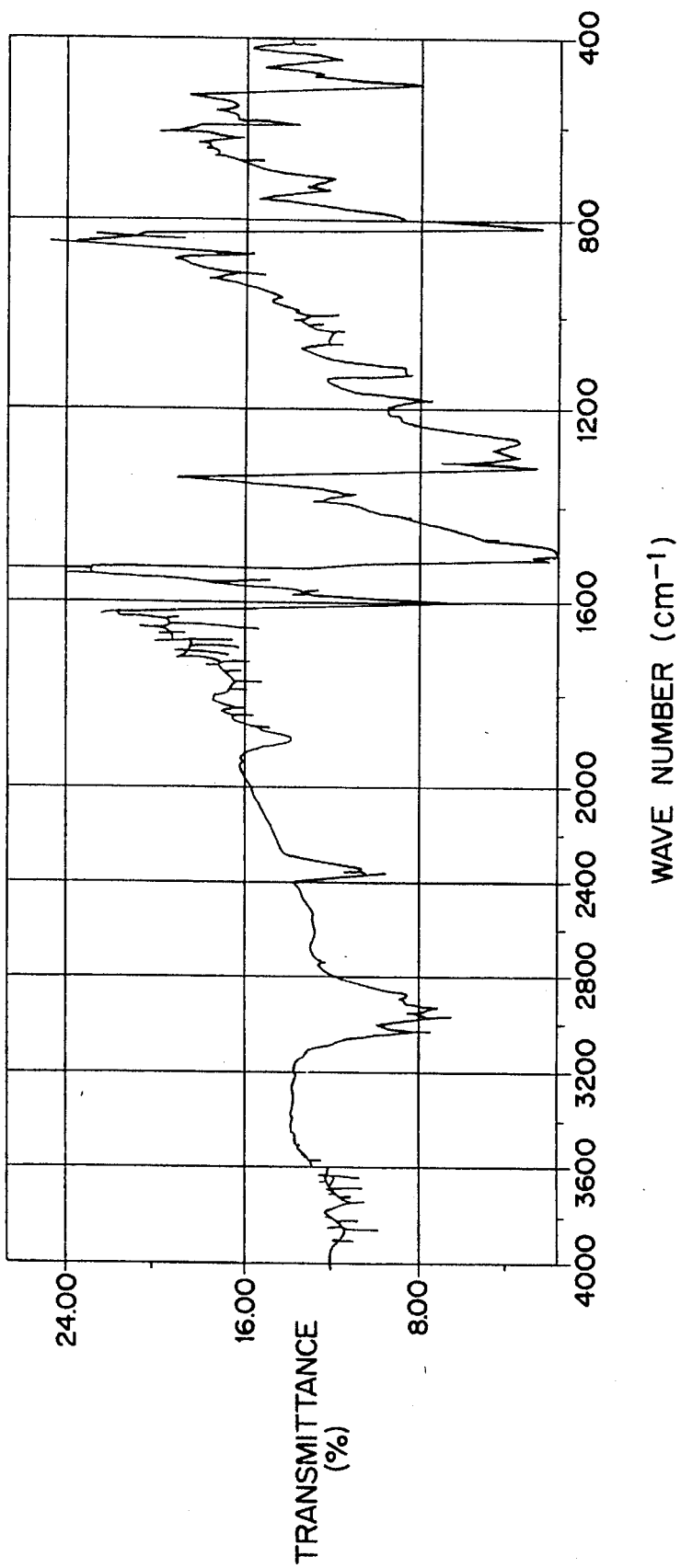

The results of the infrared spectroscopic analysis of the above compound 6-c are shown in FIG. 11.

Elemental analysis (%), Calcd.: C, 89.32; H, 6.96; N, 3.72
Found: C, 88.99; H, 6.90; N, 3.90

Melting point: 135.6° C.

Synthesis Example 29

According to the same manner as that described in Synthesis Example 28 except for using 4-iodobiphenyl in place of 4-ethyl-4'-iodobiphenyl, N,N'-di-p-tolyl-N,N'-di(biphenyl-4-yl)-3,3'-dimethylbenzidine (hereinafter referred to as 6-a) was obtained.

Melting point: 181.5° C.

Synthesis Example 30

According to the same manner as that described in Synthesis Example 28 except for using 4-methyl-4'-iodobiphenyl in place of 4-ethyl-4'-iodobiphenyl, N,N'-di-p-tolyl-N,N'-di(4-methylbiphenyl-4'-yl)-3,3'-dimethylbenzidine (hereinafter referred to as 6-b) was obtained.

Melting point: 168.3° C.

Examples 109 to 111

(Single-layer type electrophotosensitive material for digital light source)

According to the same manner as that described in Example 1 except for using a benzidine derivative shown in Table 19 as the hole transferring material (HTM), a single-layer type electrophotosensitive material for digital light source was obtained. The resulting electrophotosensitive materials were subjected to the initial electrical characteristics test (I), and their characteristics were evaluated. The results are shown in Table 19. Further, the test results of electrophotosensitive materials using benzidine derivatives (13) and (18) are also shown, for comparison.

TABLE 19

|  | HTM | $V_L$ (V) | $E_{1/2}$ (μJ/cm²) |
|---|---|---|---|
| Example 109 | 6-a | 198 | 0.81 |
| Example 110 | 6-b | 182 | 0.72 |
| Example 111 | 6-c | 178 | 0.70 |
| Comp. Example 1 | (13) | 218 | 0.90 |
| Comp. Example 6 | (18) | 245 | 1.17 |

Examples 112 to 120

(Single-layer type electrophotosensitive material for analogue light source) According to the same manner as that described in Example 11 except for using a benzidine derivative described in Table 20 as the hole transferring material (HTM), a single-layer type electrophotosensitive material for analogue light source was produced. The resulting single-layer type electrophotosensitive materials of the respective Examples and Comparative Examples were subjected to the same initial electrical characteristics test (II) as that of Example 11, and their characteristics were evaluated. The results are shown in Table 20.

TABLE 20

|  | HTM | CGM | $V_L$ (V) | $E_{1/2}$ (μJ/cm²) |
|---|---|---|---|---|
| Example 112 | 6-a | CG-1 | 184 | 3.81 |
| Example 113 | 6-b | CG-1 | 160 | 3.20 |
| Example 114 | 6-c | CG-1 | 152 | 3.24 |
| Comp. Example 8 | (13) | CG-1 | 202 | 4.25 |

TABLE 20-continued

| | HTM | CGM | $V_L$ (V) | $E_{1/2}$ (μJ/cm$^2$) |
|---|---|---|---|---|
| Comp. Example 26 | (18) | CG-1 | 237 | 5.63 |
| Example 115 | 6-a | CG-2 | 182 | 3.81 |
| Example 116 | 6-b | CG-2 | 162 | 3.19 |
| Example 117 | 6-c | CG-2 | 154 | 3.21 |
| Comp. Example 11 | (13) | CG-2 | 210 | 4.32 |
| Comp. Example 28 | (18) | CG-2 | 240 | 5.63 |
| Example 118 | 6-a | CG-3 | 187 | 3.84 |
| Example 119 | 6-b | CG-3 | 160 | 3.22 |
| Example 120 | 6-c | CG-3 | 156 | 3.23 |
| Comp. Example 14 | (13) | CG-3 | 220 | 4.41 |
| Comp. Example 30 | (18) | CG-3 | 239 | 5.64 |

What is claimed is:

1. A benzidine derivative represented by the general formula (1):

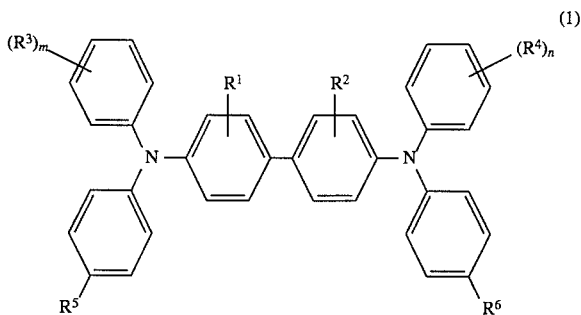

wherein $R^1$ and $R^2$ are the same or different and indicate a hydrogen atom or an alkyl group; $R^3$ and $R^4$ are the same or different and indicate an alkyl group, an alkoxy group or a halogen atom; $R^5$ and $R^6$ are the same or different and indicate an alkyl group having 3 to 5 carbon atoms or an aryl group which may contain a substituent; and m and n are the same or different and indicate an integer of 2 or 3.

2. A benzidine derivative according to claim 1, which is represented by the general formula (1'):

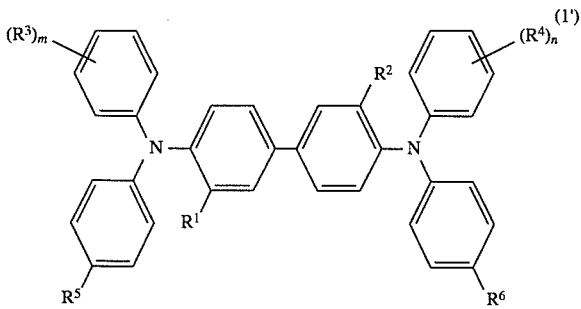

wherein $R^1$, $R^2$, $R^3$, $R^4$, $R^5$, m and n are as defined in claim 1.

3. A benzidine derivative represented by the general formula (2):

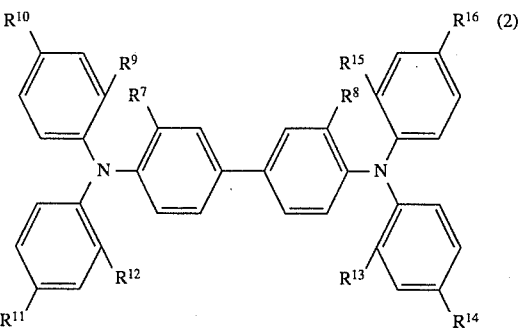

wherein $R^7$ and $R^8$ are the same or different and indicate an alkyl group, an alkoxy group or a halogen atom; and $R^9$, $R^{10}$, $R^{11}$, $R^{12}$, $R^{13}$, $R^{14}$, $R^{15}$, and $R^{16}$ are the same or different and indicate an alkyl group, an alkoxy group or a halogen atom.

4. A benzidine derivative represented by the general formula (3);

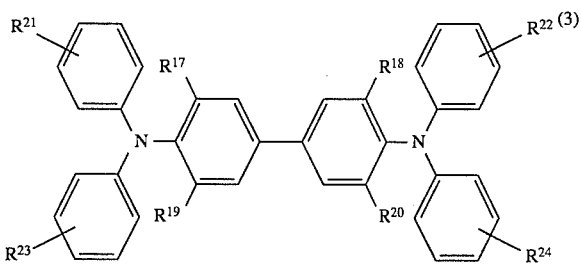

wherein $R^{17}$, $R^{18}$, $R^{19}$, and $R^{20}$ are the same or different and indicate an alkyl group or an alkoxy group; $R^{21}$ and $R^{22}$ are the same or different and indicate a hydrogen atom, an alkyl group, an alkoxy group or a halogen atom; and $R^{23}$, and $R^{24}$ are the same or different and indicate an aryl group which may contain a substituent.

5. The benzidine derivative according to claim 4, which is represented by the general formula (3'):

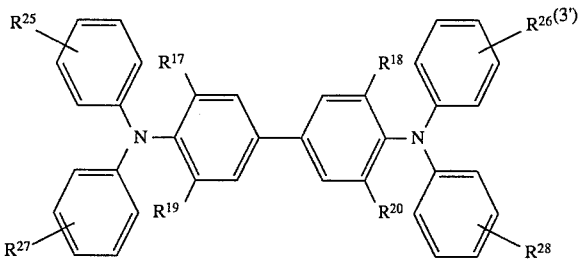

wherein $R^{17}$, $R^{18}$, $R^{19}$ and $R^{20}$ are as defined in claim 4; $R^{25}$ and $R^{26}$ are the same or different and indicate a hydrogen atom or an alkyl group; and $R^{27}$ and $R^{28}$ are the same or different and indicate an aryl group which may contain a substituent.

6. A benzidine derivative represented by the general formula (4):

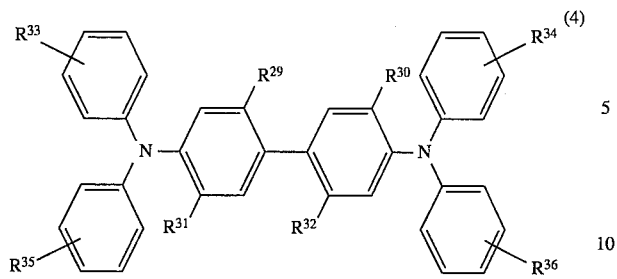

wherein $R^{29}$, $R^{30}$, $R^{31}$ and $R^{32}$ are the same or different and indicate an alkyl group or an alkoxy group; $R^{33}$ and $R^{34}$ are the same or different and indicate an alkyl group, an alkoxy group or a halogen atom; and $R^{35}$ and $R^{36}$ are the same or different and indicate an alkyl group having 3 to 5 carbon atoms.

7. A benzidine derivative represented by the general formula (5):

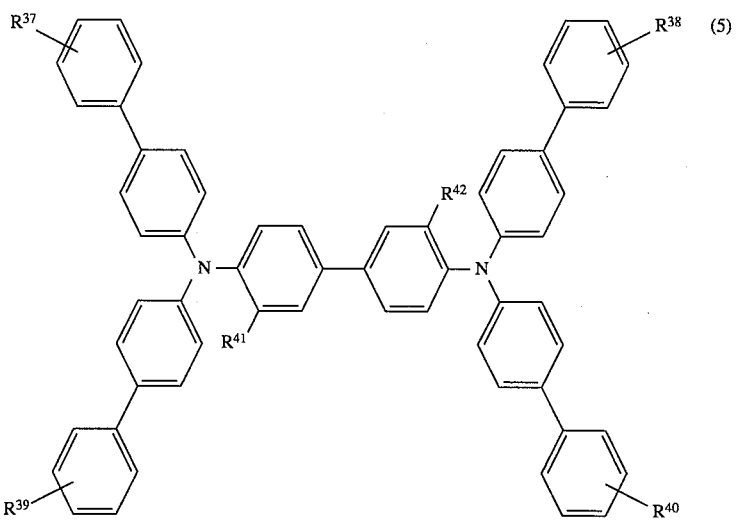

wherein $R^{37}$, $R^{38}$, $R^{39}$ and $R^{40}$ are the same or different and indicate a hydrogen atom or an alkyl group; and $R^{41}$ and $R^{42}$ are the same or different and indicate an alkyl group.

8. A benzidine derivative according to claim 1 where $R^5$ and $R^6$ are an aryl group.

9. A benzidine derivative according to claim 1 where $R^5$ is an aryl group.

* * * * *